US008814922B2

United States Patent
Hennings et al.

(10) Patent No.: US 8,814,922 B2
(45) Date of Patent: *Aug. 26, 2014

(54) METHOD FOR TREATMENT OF FINGERNAIL AND TOENAIL MICROBIAL INFECTIONS USING INFRARED LASER HEATING AND LOW PRESSURE

(75) Inventors: David R. Hennings, Roseville, CA (US); Guillermo Aguilar, Roseville, CA (US)

(73) Assignee: New Star Lasers, Inc., Roseville, CA (US)

( * ) Notice: Subject to any disclaimer, the term of this patent is extended or adjusted under 35 U.S.C. 154(b) by 549 days.

This patent is subject to a terminal disclaimer.

(21) Appl. No.: 12/841,110

(22) Filed: Jul. 21, 2010

(65) Prior Publication Data

US 2011/0172586 A1    Jul. 14, 2011

Related U.S. Application Data

(60) Provisional application No. 61/227,739, filed on Jul. 22, 2009.

(51) Int. Cl.
*A61N 5/06* (2006.01)
*A61B 18/02* (2006.01)
*A61B 18/00* (2006.01)
*A61N 5/067* (2006.01)

(52) U.S. Cl.
CPC ......... *A61N 5/0624* (2013.01); *A61N 2005/063* (2013.01); *A61N 2005/0659* (2013.01); *A61B 2018/00041* (2013.01); *A61B 18/0218* (2013.01); *A61B 2018/00452* (2013.01); *A61N 2005/067* (2013.01)
USPC ........................... 607/88; 128/898

(58) Field of Classification Search
USPC ............................ 606/9; 607/88, 89; 128/898
See application file for complete search history.

(56) References Cited

U.S. PATENT DOCUMENTS

| | | | |
|---|---|---|---|
| 5,814,040 | A | 9/1998 | Nelson et al. |
| 5,820,626 | A | 10/1998 | Baumgardner et al. |
| 5,885,274 | A | 3/1999 | Fullmer et al. |
| 5,947,956 | A | 9/1999 | Karell |
| 5,968,034 | A | 10/1999 | Fullmer et al. |
| 5,976,123 | A | 11/1999 | Baumgardner et al. |

(Continued)

FOREIGN PATENT DOCUMENTS

| | | |
|---|---|---|
| GB | 2336545 | 10/1999 |
| JP | 04-322668 | 11/1992 |

(Continued)

OTHER PUBLICATIONS

Aguilar et al., Effect of vacuum and thermal shock on laser treatment of *Trichophyton rubrum* (toenail fungus), 2010.

(Continued)

*Primary Examiner* — Lynsey Crandall
*Assistant Examiner* — Nathan J Jenness
(74) *Attorney, Agent, or Firm* — Ray K. Shahani, Esq.; Leo H. K. Lai

(57) ABSTRACT

A method of treating microbial infections, which consists of the steps of sequentially and repeatedly irradiating the microbe with continuous or pulsed infrared radiation and continuous or pulsed cooling such that heat and cold alternatively penetrates to the site of the infection in order to inactivate the pathogen.

9 Claims, 17 Drawing Sheets

(56) References Cited

U.S. PATENT DOCUMENTS

| | | | |
|---|---|---|---|
| 6,024,703 | A | 2/2000 | Zanelli et al. |
| 6,090,788 | A | 7/2000 | Lurie |
| 6,402,739 | B1 * | 6/2002 | Neev ............................ 606/9 |
| 6,413,253 | B1 | 7/2002 | Koop et al. |
| 6,451,007 | B1 | 9/2002 | Koop et al. |
| 6,663,659 | B2 | 12/2003 | McDaniel |
| 6,723,090 | B2 | 4/2004 | Altshuler et al. |
| 6,776,790 | B1 | 8/2004 | Maruyama et al. |
| 6,797,259 | B2 | 9/2004 | Rabinowitz et al. |
| 6,902,563 | B2 | 6/2005 | Wilkens et al. |
| 6,939,568 | B2 | 9/2005 | Burrel et al. |
| 6,960,201 | B2 | 11/2005 | Cumbie |
| 6,981,971 | B2 | 1/2006 | Caldera et al. |
| 6,989,023 | B2 | 1/2006 | Black |
| 7,033,381 | B1 | 4/2006 | Larsen |
| 7,137,979 | B2 | 11/2006 | Conrad et al. |
| 7,153,298 | B1 | 12/2006 | Cohen |
| 7,201,925 | B2 | 4/2007 | Gillis |
| 7,217,265 | B2 | 5/2007 | Hennings et al. |
| 7,273,478 | B2 | 9/2007 | Appling et al. |
| 7,292,893 | B2 | 11/2007 | Hoenig et al. |
| 7,306,620 | B2 | 12/2007 | Cumbie |
| 7,311,722 | B2 | 12/2007 | Larsen |
| 7,351,252 | B2 | 4/2008 | Altshuler et al. |
| 7,367,341 | B2 | 5/2008 | Anderson et al. |
| 7,373,254 | B2 | 5/2008 | Pierce |
| 7,381,427 | B2 | 6/2008 | Ancira et al. |
| 7,470,124 | B2 | 12/2008 | Bornstein |
| 7,494,502 | B2 | 2/2009 | Cumbie |
| 7,537,605 | B2 | 5/2009 | Li et al. |
| 7,572,028 | B2 | 8/2009 | Mueller et al. |
| 7,597,692 | B2 | 10/2009 | Weaver et al. |
| 7,637,930 | B2 | 12/2009 | Li et al. |
| 7,662,176 | B2 | 2/2010 | Skiba et al. |
| 2002/0169442 | A1 | 11/2002 | Neev |
| 2003/0055413 | A1 | 3/2003 | Altshuler et al. |
| 2003/0153962 | A1 | 8/2003 | Cumbie |
| 2003/0181847 | A1 | 9/2003 | Bruno-Raimondi |
| 2003/0216719 | A1 | 11/2003 | Debenedictis et al. |
| 2004/0093042 | A1 | 5/2004 | Altshuler et al. |
| 2004/0126272 | A1 | 7/2004 | Bornstein |
| 2004/0156743 | A1 | 8/2004 | Bornstein |
| 2004/0197280 | A1 | 10/2004 | Repka |
| 2004/0249426 | A1 | 12/2004 | Hoenig et al. |
| 2005/0038375 | A1 | 2/2005 | Nitzan et al. |
| 2005/0137654 | A1 | 6/2005 | Hoenig et al. |
| 2005/0215987 | A1 | 9/2005 | Slatkine |
| 2006/0004425 | A1 | 1/2006 | Cumbie |
| 2006/0079948 | A1 | 4/2006 | Dawson |
| 2006/0212098 | A1 | 9/2006 | Demetriou et al. |
| 2006/0259102 | A1 | 11/2006 | Slatkine |
| 2006/0293722 | A1 | 12/2006 | Slatkine et al. |
| 2007/0038201 | A1 | 2/2007 | Koop et al. |
| 2007/0197884 | A1 | 8/2007 | Bornstein |
| 2008/0021370 | A1 | 1/2008 | Bornstein |
| 2008/0031960 | A1 * | 2/2008 | Wilson et al. ............... 424/489 |
| 2008/0131968 | A1 | 6/2008 | Bornstein |
| 2008/0234786 | A1 * | 9/2008 | Cumbie ........................ 607/88 |
| 2009/0143842 | A1 * | 6/2009 | Cumbie et al. ............... 607/88 |
| 2009/0281537 | A1 * | 11/2009 | Britva et al. ................. 606/33 |
| 2011/0060322 | A1 * | 3/2011 | Manstein ....................... 606/9 |
| 2011/0152979 | A1 * | 6/2011 | Driscoll et al. .............. 607/93 |

FOREIGN PATENT DOCUMENTS

| | | |
|---|---|---|
| WO | WO 92/16338 | 10/1992 |
| WO | WO 97/37723 | 10/1997 |
| WO | WO 99/04628 | 2/1999 |
| WO | WO 99/27863 | 6/1999 |
| WO | WO 02/053050 | 7/2002 |
| WO | WO 03/068310 | 8/2003 |
| WO | WO 2004/000150 | 12/2003 |
| WO | WO 2004/086947 | 10/2004 |
| WO | WO 2005/046793 | 5/2005 |
| WO | WO 2006/076506 | 7/2006 |

OTHER PUBLICATIONS

Landsman, et al., Treatment of Mild, Moderate, and Severe Onychomycosis Using 870- and 930-nm Light Exposure, Journal of the American Podiatry Association, 2010, 100(3): p. 166-177.

Anvari et al., A theoretical study of the thermal response of skin to cryogen spray cooling and pulsed laser irradiation: implications for treatment of port wine stain birthmarks. Phys. Med. Biol. 40 (1995):p. 1451-1465.

Anvari et al., Dynamic Epidermal Cooling in Conjunction with Laser Treatment of Port-Wine Stains: Theoretical and Preliminary Clinical Evaluations. Lasers in Medical Science, 10:p. 105-112.

Anvari et al., Selective cooling of biological tissues: application for thermally mediated therapeutic procedures. Phys. Med. Biol. 40 (1995):p. 241-252.

Apfelberg, D.B., et al., Efficacy of the carbon dioxide laser in hand surgery. Annals of plastic surgery, 1984. 13(4): p. 320.

Woodfolk, J.A., Allergy and dermatophytes. Clinical microbiology reviews, 2005. 18(1): p. 30.

Aruthur G. Knight, The Effect of Temperature and Humidity on the Growth of *Trichophyton mentagrophytes* Spores on Human Stratum Corneum in vitro. Clinical and Experimental Dermatology (1976)I, 159.

Baker, M. and P. Jeffries, Use of commercially available cryogenic vials for long-term preservation of dermatophyte fungi. Journal of Clinical Microbiology, 2006. 44(2): p. 617.

Wright, L.R., E.M. Scott, and S.P. Gorman, Spore differentiation in a clinical strain of *Trichophyton mentagrophytes* . Microbios, 1984. 39(156): p. 87.

Wessel et al., Hydration of human nails investigated by NIR-FT-Raman spectroscopy. Biochimica et Biophysica Acta 1433 (1999):p. 210-216.

Bornstein et al., Near-infrared Photoinactivation of Bacteria and Fungi at Physiologic Temperatures. Photochemistry and Photobiology, 2009, 85:p. 1364-1374.

Sinski, J.T., B.M. Wallis, and L.M. Kelley, Effect of storage temperature on viability of *Trichophyton mentagrophytes* in infected guinea pig skin scales. Journal of Clinical Microbiology, 1979. 10(6): p. 841.

Calzavara-Pinton, P.G., M. Venturini, and R. Sala, A comprehensive overview of photodynamic therapy in the treatment of superficial fungal infections of the skin. Journal of Photochemistry & Photobiology, B: Biology, 2005. 78(1): p. 1-6.

Campbell, A.W., E.C. Anyanwu, and M. Morad, Evaluation of the drug treatment and persistence of onychomycosis. TheScientificWorldJOURNAL, 2004. 4: p. 760-777.

Chato, John C., Thermal Therapy of Toe Nail Fugus. HTD-vol. 368/BED-vol. 47, Proceedings of the ASME, Advances in Heat and Mass Transfer in Biotechnology-2000, ASME:p. 139-140.

Smijs et al., A novel ex vivo skin model to study the susceptibility of the dermatophyte *Trichophyton rubrum* to photodynamic treatment in different growth phases. Journal of Antimicrobial Chemotherapy (2007) 59:p. 433-440.

Smijs et al., Photodynamic Inactivation of the Dermatophyte *Trichophyton rubrum* . Photochemistry and Photobiology, 2003, 77(5):p. 556-560.

Coelho, L.M., et al., In vitro antifungal drug susceptibilities of dermatophytes microconidia and arthroconidia. Journal of Antimicrobial Chemotherapy, 2008. 62(4): p. 758.

Szepietowski, J.C. and J. Salomon, Do fungi play a role in psoriatic nails? Mycoses, 2007. 50(6): p. 437-442.

Tom, C.M. and M.P. Kane, Management of toenail onychomycosis. American Journal of Health-System Pharmacy, 1999. 56(9): p. 865.

Vural et al. "The effects of laser irradiation on *Trichophyton rubum* growth" Lasers Med Sci (2008) 23:349-353.

Knight, A.G., The effect of temperature and humidity on the growth of *Trichophyton mentagrophytes* spores on human stratum corneum in vitro. Clin Exp Dermatol, 1976. 1: p. 159-162.

(56) References Cited

OTHER PUBLICATIONS

Leng, W., et al., Proteomic profile of dormant *Trichophyton rubrum* conidia. BMC genomics, 2008. 9(1): p. 303.

Lim et al., Clinical Photomedicine, 1993:p. 28-31.

"Maude Adverse Event Report", Feb. 2009.

Elewski, B.E., Onychomycosis: pathogenesis, diagnosis, and management. Clinical microbiology reviews, 1998. 11(3): p. 415.

Espinel-Ingroff, A., D. Montero, and E. Martin-Mazuelos, Long-term preservation of fungal isolates in commercially prepared cryogenic Microbank vials. Journal of Clinical Microbiology, 2004. 42(3): p. 1257.

Evans, E.G.V., Causative pathogens in onychomycosis and the possibility of treatment resistance: a review. Journal of the American Academy of Dermatology, 1998. 38(5): p. S32-S36.

Schmit, J.C. and S. Brody, Biochemical genetics of *Neurospora crassa* conidial germination. Microbiology and Molecular Biology Reviews, 1976.

Hashimoto, et al., Survival and Resistance of *Trichophyton mentagrophytes* Arthrospores. Applied and Environmental Microbiology, Feb. 1978:p. 274-277.

Grover, C., Bansal S., Nanda S. et al., "Combination of surgical avulsion and topical therapy for single nail onychomycosis: a randomized controlled trial," Br I Dermatol 157, 364-368 (2007).

Hay, R.J., The future of onychomycosis therapy may involve a combination of approaches. British Journal of Dermatology, 2001. 145(S60): p. 3-8.

Hollemeyer et al., Proteolytic Peptide Patterns as Indicators for Fungal Infections and Nonfungal affections of human nails measured by Matrix-assisted Laser Desorption/Ionization Time-of-flight Mass Specrometry. Analytical Biochemistry 338 (2005):p. 326-331.

* cited by examiner

METHOD FOR TREATMENT OF FINGERNAIL AND TOENAIL MICROBIAL INFECTIONS USING INFRARED LASER HEATING AND LOW PRESSURE

RELATED APPLICATION(S)

This Application is a Non-Provisional application related to U.S. Provisional Patent Application Ser. No. 61/227,739 filed Jul. 22, 2009 entitled TREATMENT OF MICROBIAL INFECTIONS USING HOT AND COLD THERMAL SHOCK AND PRESSURE, which is incorporated herein by reference in its entirety, and claims any and all benefits to which it is entitled therefrom.

FIELD OF THE INVENTION

This invention relates to the treatment and inactivation of microbial infections, in particular fungal infections of the toenail by sequentially applying a source of thermal energy to the nail bed and then applying cold to the infected location to inactivate the microbe. This "thermal shock" therapy is more efficient, safer, and more effective than previous methods of using either thermal or cryogenic cold separately.

BACKGROUND OF THE INVENTION

As many as 700 million people worldwide suffer from onychomycosis or toenail fungal infections. There are many systemic, topical and herbal treatments available to treat this disease but none are truly efficacious and several have severe potential side effects. A need exists for a better cure for this widespread disease.

Optical and laser treatment of toenail fungus has been known for many years. In particular, UV light in the 100-400 nm range has proven to be able to inactivate many pathogens including the ones responsible for onychomycosis in non-thermal dosages. Unfortunately UV light has difficulty penetrating the toenail and can cause side effects in the dermis. UV light is not considered to be a successful treatment modality despite a great deal of research.

U.S. Pat. No. 6,723,090, issued Apr. 20, 2004 to Altshuler et al., U.S. Pat. No. 7,220,254, issued May 22, 2007 to Altshuler et al., US Publication No. 2006/0212098, published Sep. 21, 2006 to Demetriou et al., Non-patent publication "Laser treatment for toenail fungus", Proc. of SPIE Vol. 7161 published 2009 by Harris et al. and others have proposed using infrared radiation to thermally inactivate toenail fungus. Infrared radiation penetrates the toenail much better than UV and it has been shown that the fungus can be inactivated by raising the temperature of the pathogen to about 50° C. The problem associated with this method is that achieving the inactivation temperature in the nail bed risks damaging the surrounding dermal tissue, especially the matrix where the nail actually grows. In addition this prior art allows the use of infrared radiation with high hemoglobin absorption. Hemoglobin absorbing wavelengths can coagulate capillaries in the proximal fold and permanently damage the toenail.

U.S. Pat. No. 6,723,090, issued Apr. 20, 2004 to Altshuler et al., U.S. Pat. No. 7,220,254, issued May 22, 2007 to Altshuler et al. propose to use a cooling modality to protect the toenail during infrared laser irradiation to target the nail bed and he suggests that a pulsed laser may be superior to a continuous one.

US Publication No. 2006/0212098, published Sep. 21, 2006 to Demetriou et al. suggests the use of pulsed cryogen cooling, which is also described in U.S. Pat. No. 5,814,040, issued Sep. 29, 1998 to Nelson et al., to protect the toe from excessive heating and to use the process of selective photothermolysis, which is disclosed in non-patent publication "Selective Photothermolysis: Precise Microsurgery by Selective Absorption of Pulsed Radiation", published on Science, 220:524-527, 1983 by Anderson et al., to choose the correct pulse length to match the thermal properties of the fungus itself. Methods taught respectively in U.S. Pat. Nos. '090, '254 to Altshuler et al. and US Publication '098 by Demetriou et al. all require relatively high target temperatures that can damage the matrix and teach to cool only the surrounding tissue. The above-mentioned methods may cause permanent damage to sensitive areas.

U.S. Pat. No. 6,090,788, issued Jul. 18, 2000 to Lurie teaches that light-absorbing substances may be considered to induce and enhance selective photothermal damage. The problem and shortcoming with this method is the difficulty in getting the substance infused to the proper areas and the high temperatures required to inactivate the microbe. Damage to the surrounding tissue is likely to happen by using this method.

Non-patent publication "Method for disruption and re-canalization of atherosclerotic plaques in coronary vessels with photothermal bubbles generated around gold nanoparticles", published on Lasers Surg Med, 2009. 41(3): p. 240-7 by Lukianova-Hleb, E. Y., A. G. Mrochek, and D. O. proposes a non-thermal mechanical and localized removal of plaque tissue with photothermal microbubbles—PTMB to re-canalize occluded arteries without collateral damage using gold nano particles—GNP. It also teaches that users can induce non-thermal damage to locally remove unwanted tissue by producing PTMB using GNP as a catalyzer. This method however has not been proven to be efficient enough to be practical in removing large volumes of plaque buildup.

Non-patent publication "Laser surgery of port wine stains using local vacuum pressure: Changes in skin morphology and optical properties (Part I)", published on Lasers Surg Med, 2007. 39(2): p. 108-17 by Childers et al. proposes that mild vacuum pressures applied to the skin surface causes changes in morphology and its optical properties. These changes may be used for more efficient photothermolysis of small Port Wine Stain blood vessels. The vacuum suggested by Childers et al. however works primarily on blood vessels in the dermis.

ADVANTAGES AND SUMMARY OF THE INVENTION

The present invention makes the treatment of microbial infections much more effective and efficient than previously taught in the prior art.

Target thermal feedback has been used in the prior art, such as in the laser treatment devices of Koop et al., but has not been considered in the treatment of onychomycosis or other fungal or microbial infections because of the difficulty of obtaining consistent thermal readings from low emissivity targets like a toenail. Since the toenail has a very low water content, its emissivity is much lower than the dermis. Therefore, it has been unexpectedly found that use of a thermal sensor designed to work on tissue would also work on the toenail. It would not be obvious that a correlation between the surface temperature of the nail and the nail bed exists or that the thermal response time of the detector can be made fast enough to control a laser to prevent overheating of the tissue. Nor would it be obvious that thermal feedback can be made to work in a sequential mode with aggressive cooling fluids such as but not limited to cold air, chilled water, refrigerant and/or cryogen spray cooling. It is not obvious that a thermal detector can also measure and control cooling. Automatic target thermal feedback prevents over or under treatment that is inherent in the prior art.

The present invention uses the process of thermal shock to help inactivate the fungus. Either heat or cold by themselves are effective at inactivating pathogens but rapid changes of temperature are even more effective in inactivating pathogens and are more tolerable by surrounding tissue. The present invention therefore uses rapid cooling to cool the target tissue followed by rapid heating of the target tissue or vice versa. Prior art teaches against cooling the target tissue because it then takes much more thermal energy to overcome the cold and heat the target to effective temperatures. Prior art teaches to only cool surrounding or overlaying tissue and to avoid cooling the pathogen itself or the target area. This is because prior art assumes the target tissue damage has to be induced by high temperatures and cooling is only an auxiliary procedure to prevent excessive heating. Our invention inactivates the pathogen with low and high extreme temperatures far more effectively and efficiently than the use of either one alone, thus making the procedure much more efficient and safer. It also allows for a temporary change of mechanical, thermal and optical properties, e.g., as the fungus freezes during a pre-cooling procedure it turns icy which results in more scattering, which makes it more susceptible to absorption from the subsequent laser irradiation in the visible and IR spectra and also more brittle, which also makes it more susceptible to subsequent mechanical deformation. This invention will inactivate microbes at lower heating temperatures making it safer and less painful than prior art.

The present invention uses mechanical deformation, such as induced by mechanical pressure, to disrupt mechanically the fungal bed once it has been frozen. Cooling in the form of a spray onto the target nail surface works optimally in conjunction with steady or pulsed infrared laser irradiation with a pulse length chosen to be selectively absorbed by the fungus. No prior art has suggested that cold application be used therapeutically to inactivate microbes. This invention will allow the inactivation of microbes with less energy applied causing less pain and chance of damage to surrounding tissue.

The present invention uses localized and temporary external vacuum pressure through the use of a transparent toe jacket. This jacket seals around the toe and is instrumented with a vacuum pump to lower the atmospheric pressure around it, optionally including the toenail-fungus-toe space, prior to treatment. By doing so, the boiling temperature of either the existing moisture within the fungus bed or of a previously diffused water-based solution is diminished proportionally, requiring the use of lower laser fluences, but most importantly, inducing evaporation, bubble growth and subsequent bubble explosion at temperatures much lower than the threshold of tissue damage and patient pain. In fact, depending on the absolute vacuum pressure that one can achieve within the jacket, this procedure may induce the formation of cavitation bubbles underneath the toenail with minimal or even without the need for laser heating, e.g., IPL. Thus, this combined mechanism adds the potential of inducing localized mechanical ablation to the thermal ablation induced by the laser or IPL. This invention allows the inactivation of microbes with much less energy applied making it more effective and safer.

The present invention adds highly absorbing dyes and/or metallic nanoparticles such as gold nanoparticles GNP to enhance the absorption by the targeted fungus. This approach also benefits from the combined application of vacuum pressure to induce cavitation and lower the threshold for nucleation of evaporation bubbles and thus the temperature of the treated area. Furthermore, the use of GNP causes photothermal micro-bubbles PTMB at the surface of the GNP, which in turn provide an effective way of promoting non-thermal mechanical and localized inactivation of microbes. Prior art has not taught the use of GNP to inactivate living microbes. Prior art has only utilized GNP to physically ablate nonliving tissue such as plaque.

The present invention uses positive pressure on the toe or toe nail against each other with the objective to temporarily "blanch" the subjacent skin from blood supply. The intent is to temporarily remove blood perfusion to this region and thus reduce the concentration of competing absorbers, i.e., hemoglobin, for the subsequent laser or IPL irradiation. This "blanching" effect occurs within the first 0.5 sec after pressure is applied onto the skin. After that time, blood perfusion returns and even increases within that region. Depending on the wavelength(s) used for this purpose, it is beneficial to the procedure to wait longer than 0.5 sec to have a back absorber underneath the fungus bed which can serve as a heat source for prolonged heating of the fungus. This invention will reduce the energy needed to inactivate the microbe making the procedure much safer and more effective. Prior art does not teach to cycle the pressure on the target. The use of positive pressure will force the blood out of small capillaries in the matrix of the nail. Lasers and energy sources with wavelengths that are absorbed in hemoglobin such as those from Intense pulsed light systems and lasers with wavelengths in the visible and near infrared from 400 nm to 1100 nm can then be safely used, and when treating only the nail bed the subsequent perfusion will enhance the energy absorption in this area resulting in a more efficient treatment.

Thus, it is an object of the present invention to make the treatment of microbial infections much more effective and efficient.

It is yet a further object of the present invention to provide treatment of microbial infections using laser energy transmitted via fiber optic laser delivery device.

It is yet a further object of the present invention to provide an improved method and apparatus for treatment of microbial infections of toenails, including onychomycosis.

DETAILED DESCRIPTION OF THE PREFERRED EMBODIMENT

Figure 1:
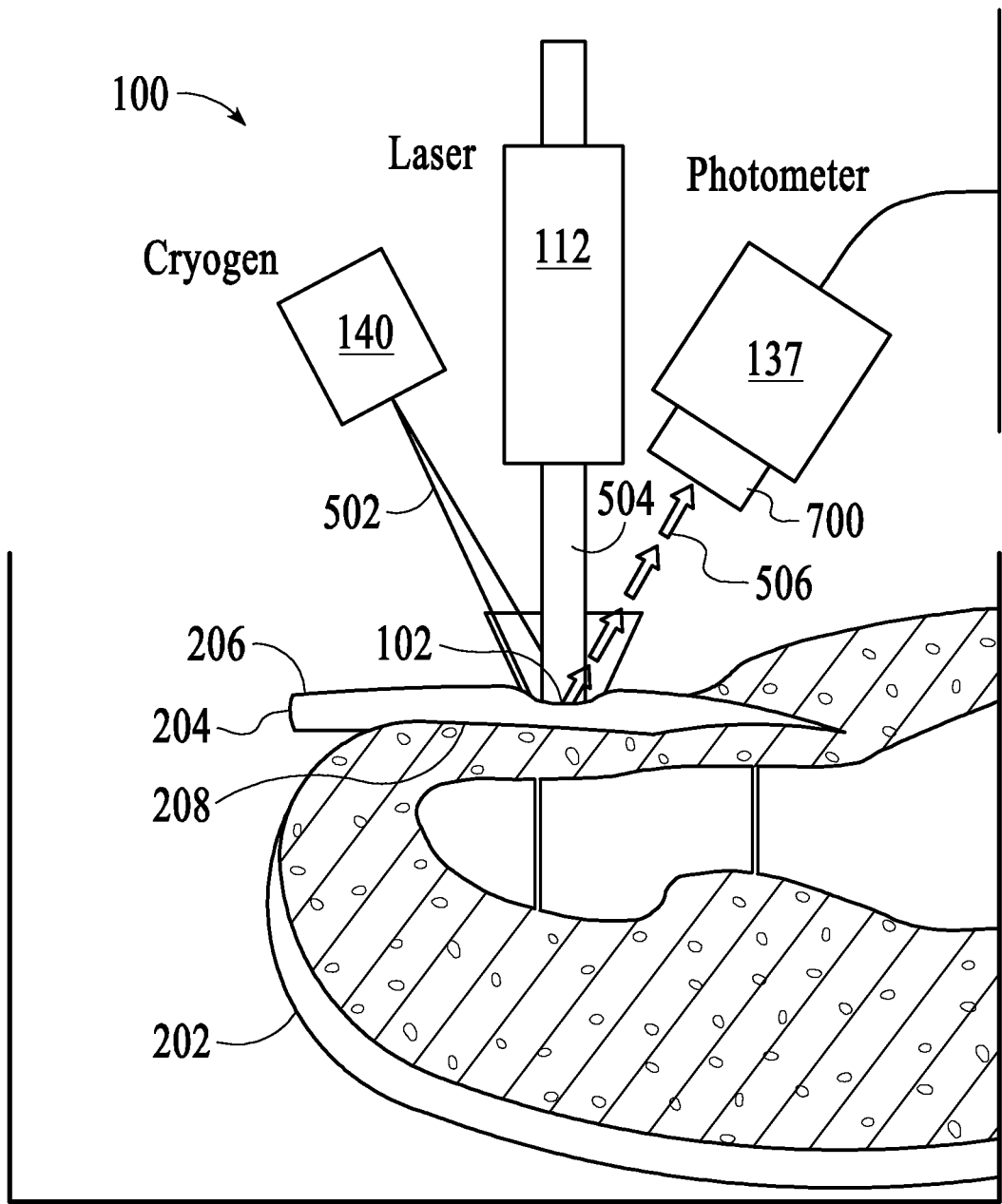
FIG. 1 is a representative illustration showing an embodiment of the apparatus and method of treatment of microbial infections using hot and cold thermal shock and pressure 100 of the present invention.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

FIG. 1 is a representative illustration showing an embodiment of the apparatus and method of treatment of microbial infections using hot and cold thermal shock and pressure 100 of the present invention.

The present invention uses an automatic target thermal feedback to precisely control the dosimetry of the laser 112, or intense light or intense pulsed light IPL irradiation, to prevent damage to surrounding tissue and reduce pain. A non-contact thermal detector 137, such as made by Raytek or equivalent, is built into a handpiece along with a lens to focus the laser delivery fiber optic 504 or a laser diode. The output of the non-contact thermal detector 137 is used to adjust the power output of the laser 112 to maintain a selected treatment temperature at the treatment site 102.

A preferred embodiment of the present invention utilizes a 1320 nm continuous or pulsed laser 112 that is capable of delivering 2 to 5 watts of energy, or more or less, with continuous or pulsed cryogen cooling 140. The energy is delivered from a handpiece that focuses the light into a 2-10 mm diameter spot on the treatment tissue, treatment site 102. A non contact thermal sensor 137 detects the temperature of the treated spot and send a signal to the laser 112 control system which then adjusts the energy to maintain a pre selected target temperature at the spot. A continuous or pulsed cooling spray device 140 is incorporated into the handpiece to deliver a spray of coolant 502 to the target treatment spot 102 after each laser treatment interval.

It will be understood that the site of infection is associated with the nail 204 of the finger or toe 202 the nail has a plate 206 as well as a bed 208.

Figure 2:
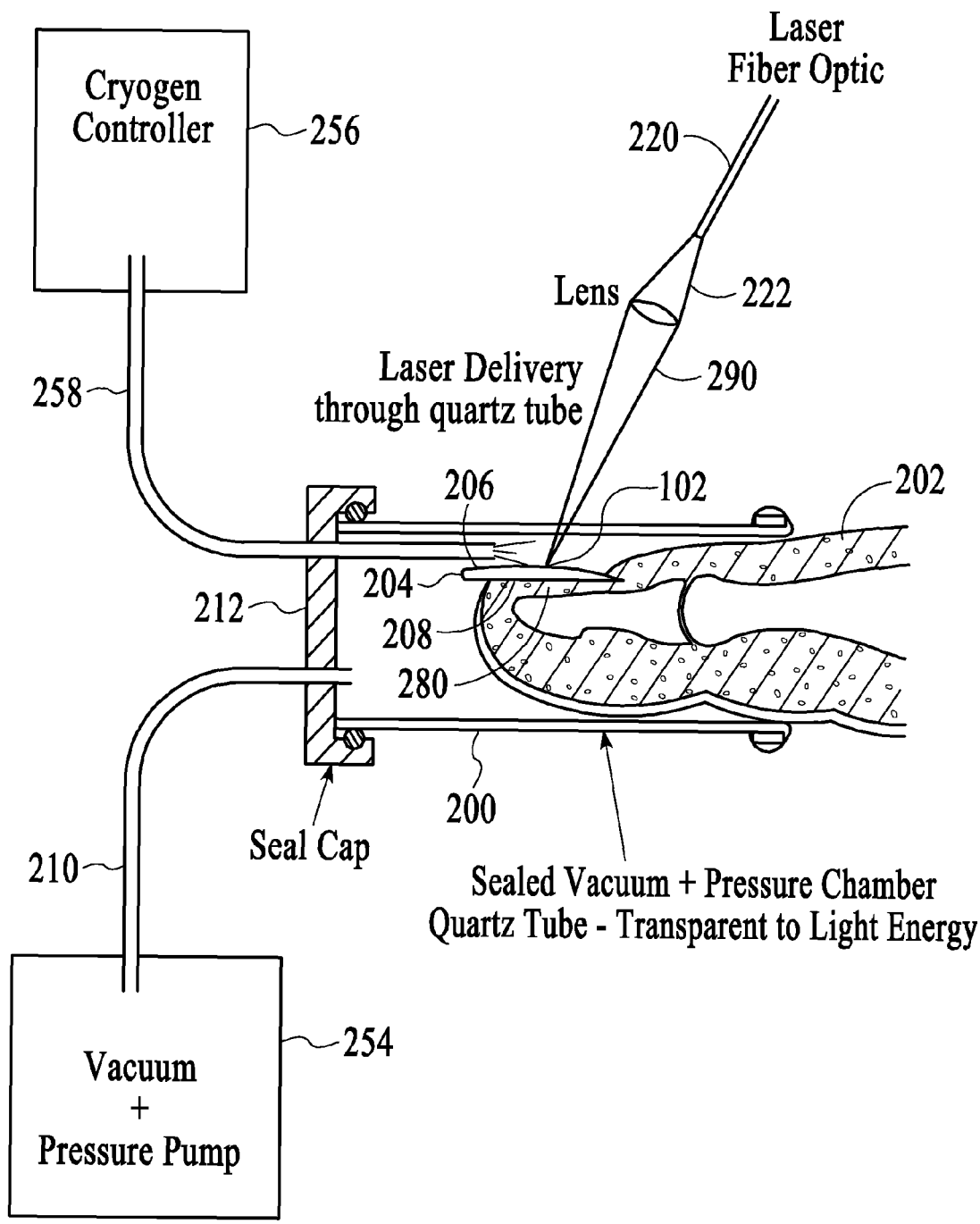
FIG. 2 is a representative illustration showing an embodiment of a transparent toe jacket 200 of the present invention 100.

FIG. 2 is a representative illustration showing an embodiment of a transparent toe jacket 200 of the present invention 100.

As described above, the present invention uses localized and temporary external vacuum pressure through the use of a transparent toe jacket 200. In one embodiment, jacket 200 is a quartz tube that is transparent to light energy, seals vacuum and acts as a pressure chamber. This jacket 200 seals around the finger or toe 202 and is instrumented with a vacuum or pressure pump 254 to lower or increase the atmospheric pressure around it, optionally including the toenail-fungus-toe space, prior to treatment. In an embodiment of the present invention, cryogenic cooling controller 256 provides such coolant via cooling supply lines 258. Cooling lines 258 and vacuum lines 210 lead through sealing cap 212 or other portion of the toe jacket 200. The toe jacket 200 provides a unique, sealed vacuum and pressure chamber made of quartz tube transparent to light energy. Laser energy can be directed to impinge directly onto the nail plate 206. It will be understood that energy not absorbed by the nail plate 206 itself will pass therethrough to the nail bed 208 and into the underlying tissue 280 of the finger or toe being treated. Preferential absorption of laser energy 290 having a wavelength 1470 nm by the nail plate 206 of the infected toe or finger nail 204 results in a controlled elevation in temperature to a temperature effective at disinfection of the infected regions or areas without causing irreversible thermal damage to the infected nails.

Fiber optic laser delivery system 220 comprises optical fibers as well as lens mechanism 222, and optional filters, convertors or other beam modifiers which can be coupled to the toe jacket 200 as desired. In an embodiment, laser energy 290 is delivered through fiber optic or other quartz tube structure 220.

Figure 3:
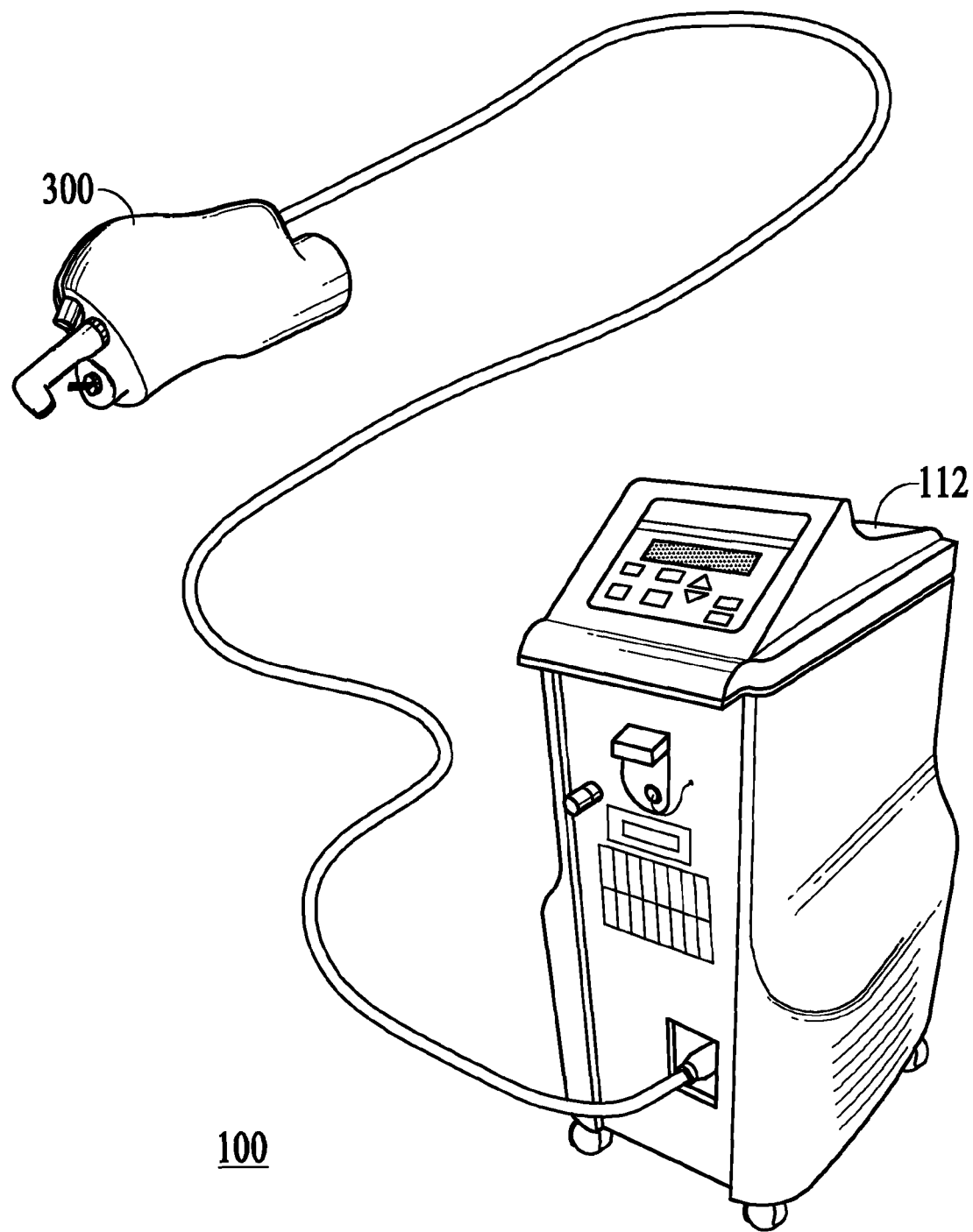
FIG. 3 is a representative illustration showing an embodiment of laser control system with cooling spray device devices and methods of the present invention 100.

FIG. 3 is a representative illustration showing an embodiment of laser control system with cooling spray device devices and methods of the present invention 100. As described above, a preferred embodiment of the present invention utilizes a 1320 nm continuous or pulsed laser 112 that is capable of delivering 2 to 5 watts of energy, with continuous or pulsed cryogen cooling. The energy is delivered from a handpiece 300 that focuses the light into a 2-10 mm diameter spot on the target treatment spot 102. The laser 112 control system adjusts the energy to maintain a pre selected target temperature at the spot. A continuous or pulsed cooling spray device is incorporated into the handpiece 300 to deliver a spray of coolant to the target treatment spot 102 after each laser treatment interval.

The laser and coolant delivery handpiece 300 can be the CoolTouch® TQ10 model handpiece or equivalent. In an embodiment, the handpiece 300 can deliver laser energy 290 at a wavelength of 1320 nanometers at a fluence rate of 24 Joules per square centimeter. The handpiece 300 with integrated continuous or pulsed cryogen cooling reduces the surface temperature for nail protection allowing the laser energy 290 to be effectively targeted. Cooling can be provided adjustably pre, mid and post cooling to maximize patient comfort, safety and efficacy.

Treatment Agents

It will be understood that THE PRESENT INVENTION consists of applying liquid or gas directly to the target, i.e., to the infected nail. Furthermore, the liquid or gas may contain one of more of the following: pain reducing agent, antifungal agent, anti-microbial agent, antiseptic agent or disinfectant agent. It will be understood that there are a wide range of agents which are associated with pain reduction, anti-irritant, antifungal treatment, antimicrobial and antibiotic activity as well as antiseptic and disinfecting properties, the use of which is expressly contemplated herein.

Antifungal agents may include any antifungal agents useful in dermatological compositions. Examples of antifungal agents include, without limitation, Tea Tree oil and other naturally occurring oils and compounds, nystatin, ciclopirox and ciclopirox olamine, griseofulvin, itraconazole, fluconazole, ketoconazole, terbinafine, econazole, benzyl alcohol, undecylenic acid and salts thereof, benzyl benzoate and combinations thereof. Antifungal agents are well known in the art. One of ordinary skill in the art would understand, appreciate and recognize agents that are considered to be antifungal agents.

Antimicrobial agents may include any antimicrobial agents useful in dermatological compositions. Antimicrobial agents include, without limitation, benzoyl peroxide, povidone iodine, hexachlorphene, chlorhexidine, mupirocin, gentimycin, neomycin, bacitracin, polymixin, erythromycin, clindamycin, metronidazole, clarithromycin, silver sulfadiazine, dapsone, zinc pyrithione, cephalosporin, thymol, mafenide acetate, nitrofurazone, generators of nitric oxide benzyl alcohol, sulfamethoxazole, sulfasalazine, sulfasoxazole, acetylsulfasoxazole and combinations thereof. Antimicrobial agents are well known in the art. One of ordinary skill in the art would understand, appreciate and recognize agents that are considered to be antimicrobial agents.

Anti-irritants are well known in the art. One of ordinary skill in the art would understand, appreciate and recognize agents that are considered to be anti-irritants. Preferred anti-irritants include but are not limited to aloe vera gel, alpha bisabolol, allantoin, sorbitol, urea, lactic acid and salts, glucose derivatives, zinc acetate, zinc carbonate, zinc oxide, potassium gluconate, dimethicone, glycerin, petrolatum, lanolin, peramides, uric acid and salts, N-acetyl cysteine, and hydrocortisone.

Disinfectants are also well known in the art. One of ordinary skill in the art would understand, appreciate and recognize agents that are considered to be disinfectants. Preferred disinfectants include but are not limited to chlorine bleach or sodium hypochlorite Method of Treatment The following is taken from the CoolBreeze® (trademark) treatment guidelines for onychomycosis.

Patient Preparation:
1. Remove all lotions and skin care products, making certain that the skin of the foot and nail bed are completely dry prior to treatment.
2. Debridement of thickened nails might be necessary prior to laser treatment
3. Topical anesthetics are not recommended for the Cool-Breeze mode. Anesthetics can interfere with the patient's ability to assess their comfort level.

Setting Treatment Parameters:
Fluence: Set at 5 Joules-Sec/cm2 (Range is 5-12 Joules-Seconds/cm2)
  Adjust as needed to achieve a comfortable treatment for the patient.
  When using higher fluences, the nail bed will reach target temperature more quickly and the speed of hand piece movement will need to be faster.
Target Temperature: Set at 39° C. (Range is 30°-42° C.)
  The system will sound an audible alert, "Beep" when the target nail bed temperature is reached, as well as displaying the temperature on the control panel.
  Each subsequent pass will increase temperature and the target temperature may be reached more quickly than anticipated.
Cryogen Cooling: Set at 40 msec (Range is 0-50 msec)
  Cryogen will be delivered after the target temperature has been achieved.
  NOTE: These guidelines are meant to establish starting parameters. In any given clinical procedure there are many variables involved, therefore the settings may need to be modified to accomplish the desired treatment goals.

The CoolBreeze® Mode
  Micro-pulses of laser energy are delivered continuously when the foot pedal is depressed.
  When the target nail bed temperature is reached, system will emit an audible high pitched, rapidly repeating, "beep". And the firing of the laser will slow.
  Target temperature is displayed continuously on the display panel.

Movement of the Hand Piece
  The speed of the hand piece movement and the selected fluence should allow the patient to experience mild to moderate warmth but not a sensation of hot or pain.
  Target temperature and the confirming audible beep will be reached quicker with each additional pass and over areas of thin or debrided nails.
  The skin of the toe should be stretched gently to flatten and move the skin surface away from the nail bed.
  Lightly glide the gold footplate across the nail surface, avoiding treatment to the surrounding skin overlap by manipulating the hand piece in a smooth continuous motion.
  Keep the hand piece perpendicular to the nail surface.
  Each pass may be changed to a different orientation of movement for a more uniform distribution of energy.
  Multiple passes will be needed before moving to the next toe.

Suggested Treatment Interval: Every Week for a Total of 3-4 Treatments
  The number of the treatments is based on the condition of the nail and the amount of improvement desired.
  Since toenails grow very slowly, the improvement is not seen immediately.
  Changes in the nail bed are cellular in nature and take time. Improvement may be seen over a period of several months as the undamaged nail grows out.

Post Procedure Care:
  Wear comfortable shoes and hosiery that allow your feet some breathing space.
  Wear shoes, sandals or flip-flops in community showers or locker rooms.
  Wash your feet every day, dry them thoroughly and use a good quality foot powder. Ask your doctor to recommend a foot powder with the right blend of ingredients.
  Wear clean socks or stockings every day.
  Keep toenails trimmed
  Disinfect pedicure tools before and after you use them. Note: Be sure to wipe the footplate with an appropriate disinfectant when finish treating each patient and before storing the handpiece.

EXPERIMENTAL RESULTS

Experiment I

Soaking the nail in a water bath or with a wet towel laid on the toes increases the hydration of the nail and improves the absorption of 1320-2100 nm laser exposure. This allows effective treatments at lower power and reduces possible injury. Pre-treatment hydration will be described and discussed in later section of the application. Many prior art assumes that the treatment energy must be transmitted through the nail to treat the fungus itself in the nail bed.

Dry nail is composed of a fibrous protein called keratin. Experiment I tests showed that the use of a 1470 nm laser required very little power to heat up a nail that has been soaked in water to get hydrated. Equivalent heating of a dry nail requires 7 watts of 1064 nm, 2 watts of 1320 nm but only 1 watt of 1470 nm. We discovered that there is an absorption peak in fibrous proteins at about 1500 nm that would explain this effect.

The present invention comprises the step of irradiating the microbe with infrared radiation using laser energy having a wavelength between about 1200 nm and about 2000 nm, and more particularly, using laser energy having a wavelength of about 1320 nm.

The present invention further comprises the step of irradiating the microbe with infrared radiation using laser energy having a wavelength between about 1450 nm and about 1550 nm, and more particularly, using laser energy having a wavelength of about 1470 nm.

Figure 4:
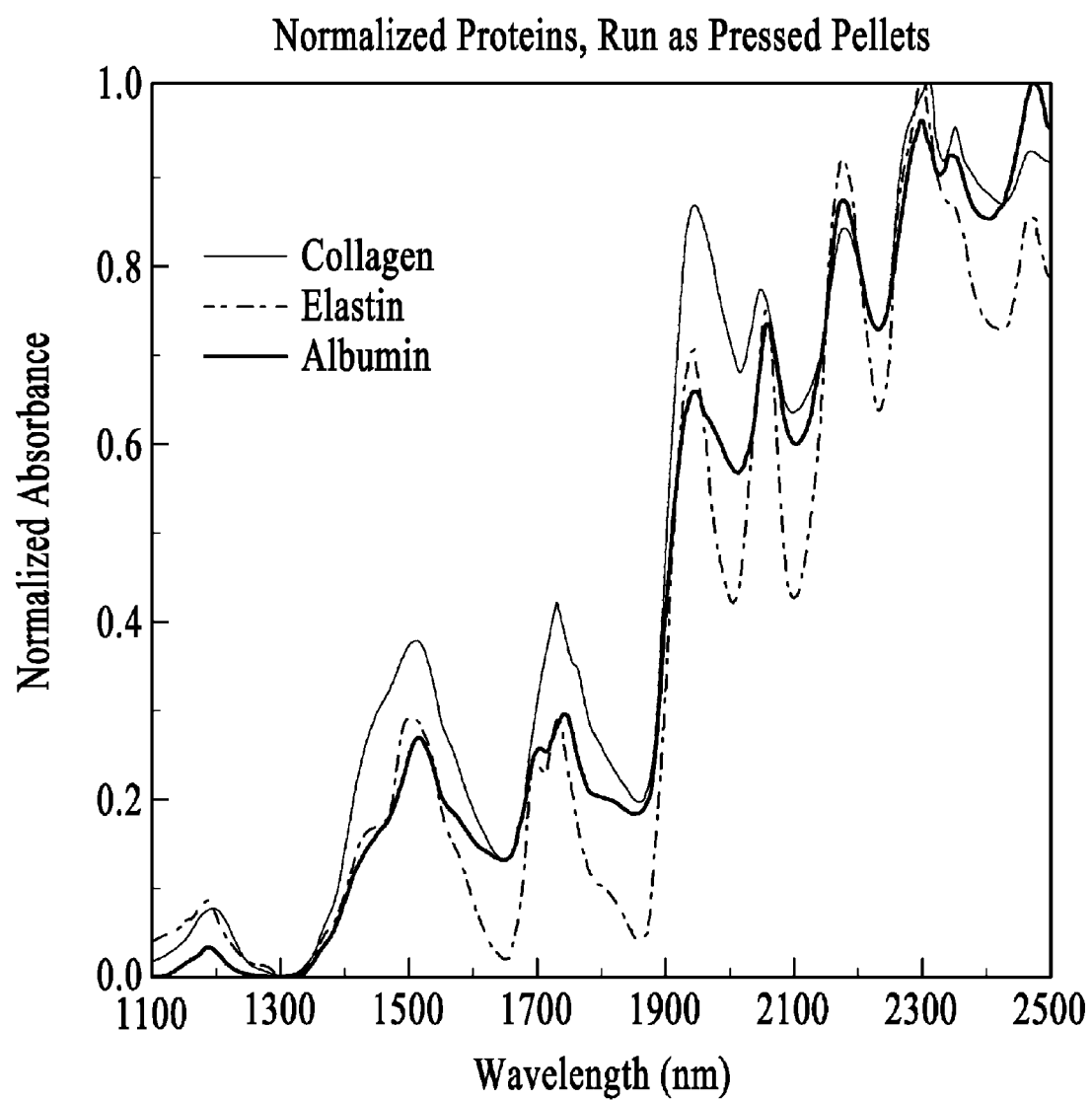
FIG. 4 is a representative chart showing an absorption curve that shows an absorption peak among similar proteins.
Figure 5:
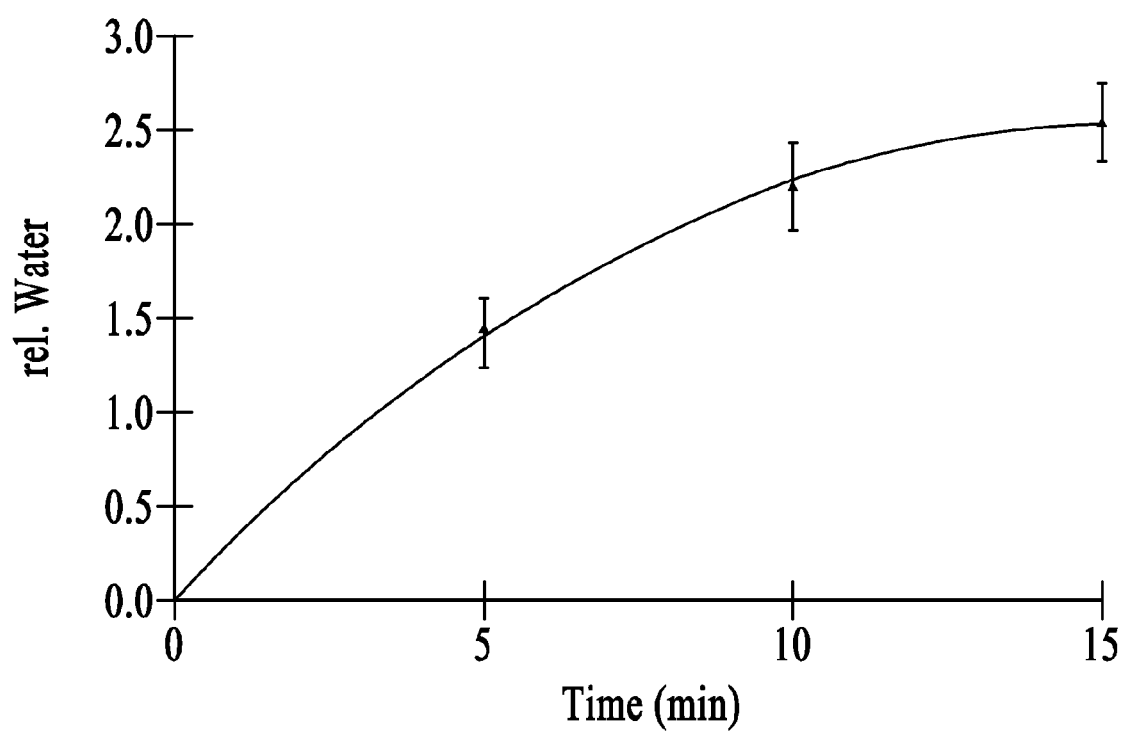
FIG. 5 is a representative chart showing time-dependent water uptake of toe nail samples (distal part).

FIG. 4 is a representative chart showing an absorption curve that shows an absorption peak among similar proteins. This is a significant new discovery and may lead to the treatment of onychomycosis with laser powers low enough to qualify for use by a non-physician and significantly lower the cost of the device.

Furthermore, there is an adverse event report to the FDA from a company that uses higher power 1064 nm lasers to treat toenails. There was blistering under the nail post operation. This is the kind of complication that can be avoided by using lower powered lasers that are more highly absorbed in the nail plate itself.

Experiment II

The CoolTouch® laser was used to treat infected large toenails in two individuals with a single treatment. New clear growth was seen at three months and the nails are completely clear at nine months post treatment. The laser was used on six Podiatry patients suffering from onychomycosis with a single treatment. At three months a band of clear nail is seen in all six patients and the site was tested and confirmed to be free of fungal infections.

Experiment III

In recent years, the eradication of Trichophyton rubrum (toenail fungus) has been attempted via laser irradiation. Researchers have recognized that this approach could result advantageous relative to oral, mechanical and chemical therapies. However, anticipating that the fluences required to achieve the necessary thermal effects on this fungus could unintentionally damage the underlying toe dermal layer, two auxiliary approaches are explored in this Experiment:

(a) laser irradiation under vacuum pressure, with and without water dousing; and (b) rapid-cooling followed by laser heating (thermal shock).

The rationale behind these two approaches is that at low pressures, the temperature necessary to achieve fungus necrotic thermal effects, e.g., water evaporation/boiling, is significantly reduced, and thus requires lower fluences. Similarly, a thermal shock induced by a cryogen-cooled tip or spurt followed by laser irradiation may require much lower fluences to achieve the desired fungus necrosis. For all the tests in Experiment III as presented herein, CoolTouch™, model CT3™ plus, 1320 nm laser was used with 50 ms pulse duration and 20 Hz to irradiate fungi colonies grown on Petri dishes.

The vacuum pressure experiments, as in Experiment a, consisted of exposing fungi colonies to a sub-atmospheric pressure of 84.7 kPa or 25 in Hg with and without water dousing for 5 minutes, followed by laser irradiation with fluence of 4.0 J/cm$^2$ and total energies ranging from 40-90 J.

The thermal shock experiments, as in Experiment b, consisted of three separate sections:

1. Control—Cooling the fungus to 0° C. at an approximate rate of 0.39° C./min and then irradiating to 45-60° C.;
2. Slow Cooling the fungus to −20° C. at a rate of 1.075° C./min and irradiating to 45° C.; and
3. Quick Cooling the fungus to −20° C. at a rate of 21.5° C./min and irradiating to 45° C.

All three types of thermal shock experiments were performed at a fluence of 4.8 J/cm$^2$. Thus far, fungus growth rate over an one week period was the only criterion used to assess the feasibility of each of these procedures. Our results indicate that both the vacuum (a) and thermal shock (b) approaches hamper the growth rate of fungi colonies relative to untreated control samples, especially the combination of water dousing or hydration prior to laser irradiation under vacuum conditions (a) and slow cooling rate preceding rapid laser irradiation for a thermal shock effect.

Figure 6:
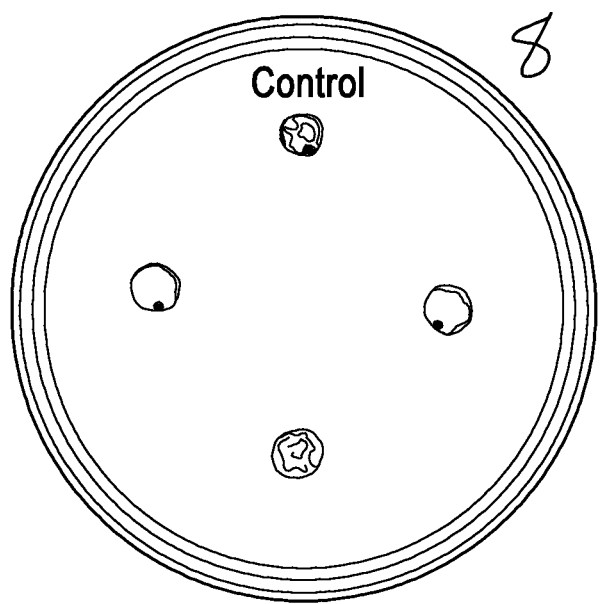
FIG. 6 is a representative illustration showing an example of plate set up with new samples of fungus.

Material and Method:

An isolate of *T. rubrum* was obtained from American Type Culture Collection (Manassas, Va.) and was cultivated on potato dextrose agar. Four-millimeter biopsy punch samples of the primary colonies were then transplanted to new plates containing pure potato dextrose agar as medium, four colonies per plate, and immediately subjected to the treatments described below. FIG. 6 is a representative illustration showing an example of plate set up with new samples of fungus. As shown in FIG. 6, a typical arrangement of the 4 fungi colonies on a Petri dish is illustrated. The number "8" refers to the experiment number for categorization purposes only. One colony of each plate was used for one of three types of controls: (1) completely untreated, (2) exposed to 84.7 kPa or 25 in Hg vacuum pressure, non-irradiated, (3) cooled to approximately 0° C., non-irradiated. All control samples were left to grow inside an incubator at 30° C. temperature with no $O_2$ or $CO_2$ control. Treated samples were also introduced into the incubator after the procedures and allowed to grow under the same conditions.

Figure 7:
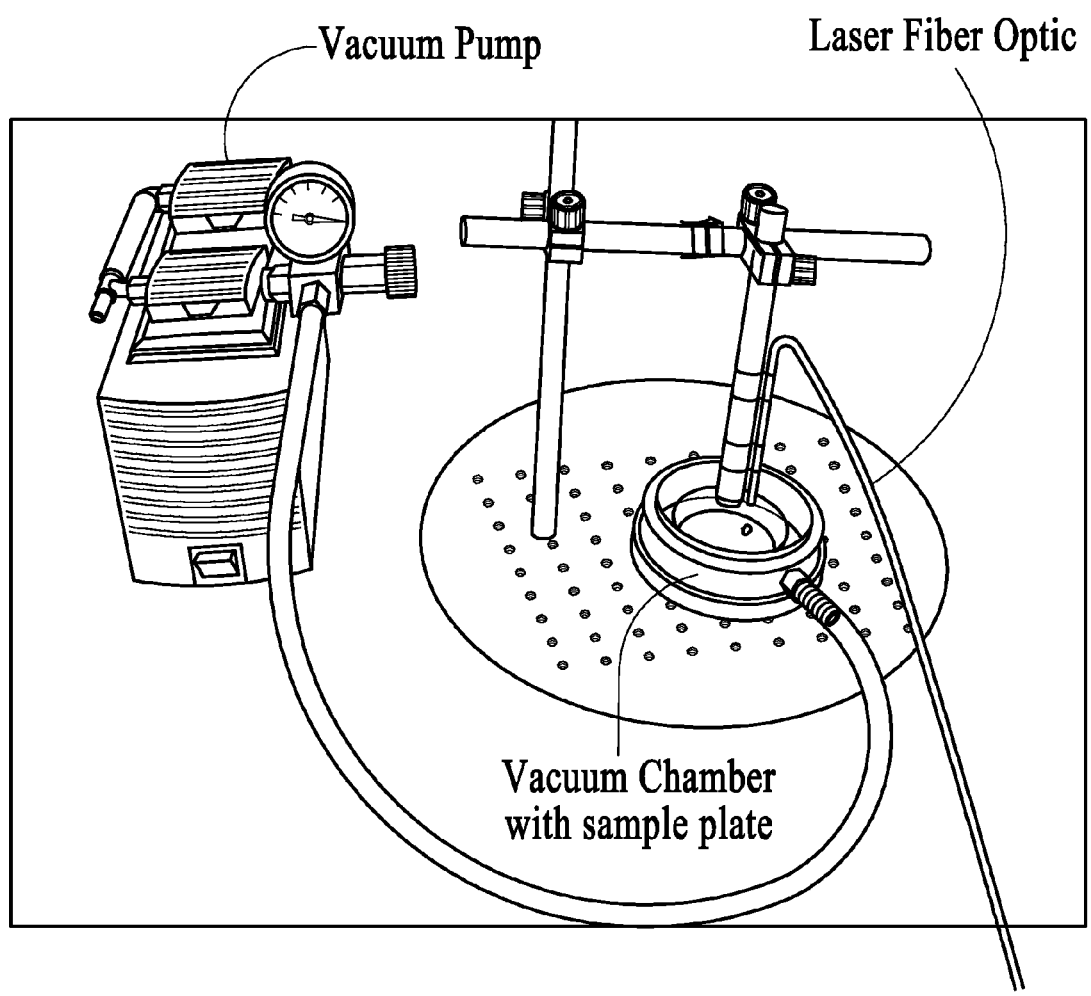
FIG. 7 is a representative illustration showing the set up for vacuum procedure.

The above-mentioned vacuum conditions (a) and thermal shock (b) procedures were as follows:

Vacuum Conditions Procedure:

FIG. 7 is a representative illustration showing the set up for vacuum conditions procedure. The vacuum-treated samples were divided into two subsets. Those denoted "V", were dry samples placed under −84.7 kPa or 25 in Hg pressure for approximately 5 minutes and subsequently exposed to laser irradiation, which was provided by a CoolTouch™ Q-switched, Nd:YAG laser, 1320 nm, 20 Hz, and 4 mm beam diameter, using a fluence of 4.0 J/cm$^2$ per pulse and an exposure time of 2-20 seconds. Those denoted "VW" followed the same procedure as "V" except that they were first heavily doused or hydrated in water before being exposed to vacuum pressure and laser irradiation. Vacuum control samples is only placed under −84.7 kPa or 25 in Hg pressure for approximately 5 minutes and not followed by laser irradiation.

Figure 8:
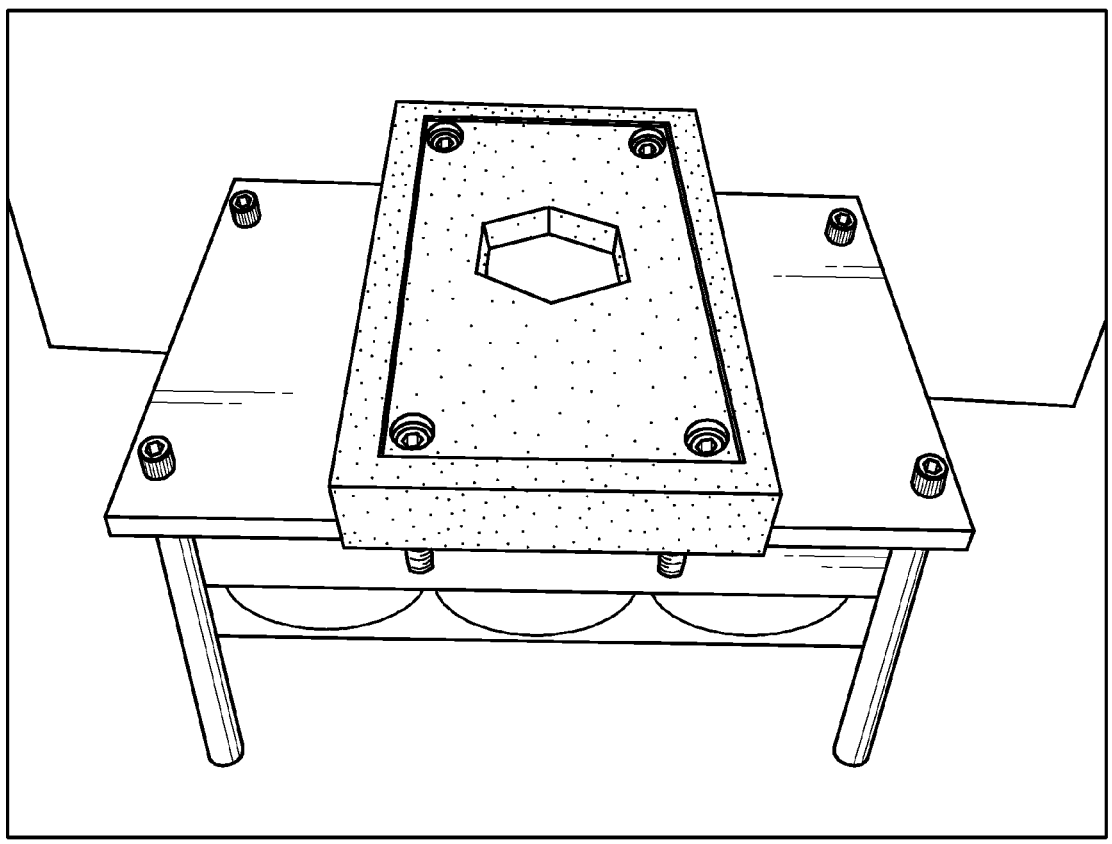
FIG. 8 is a representative illustration showing the set up of Alpha heat sinks with cooling plate surrounded by Styrofoam on top.

Thermal Shocked Procedure:

FIG. 8 is a representative illustration showing the set up of Alpha heat sinks with cooling plate surrounded by Styrofoam on top. As shown in FIG. 8, thermal shocked samples were placed on top of 2 Alpha Heatsinks and allowed to cool down following three different protocols:

Protocol Cooling Control: A subset of samples was surrounded in ice until samples were approximately 0° C. at a rate of <0.39° C./min. Proof of cooling concept samples are another subset of these samples were cooled in the same way and then irradiated as described above for approximately 7-15 seconds, until the samples reached 45-60° C.

Protocol Slow Cooling: A subset of samples was cooled down at a rate of 1.075° C./min until they reached a minimum temperature of −20° C. Then they were introduced into the incubator and allowed to be re-warm to 30° C. Slow Cooling, 1320 samples are another subset of these samples was cooled in the same way and then irradiated for approximately 2-4 seconds until a maximum temperature of 45° C. was reached.

Protocol Quick Cooling: A subset of samples was cooled down at a rate of 21.5° C./min until they reached a minimum temperature of −20° C. Then they were allowed to be re-warm to 30° C. in the incubator. Quick Cooling, 1320 samples are another subset of these samples was cooled in the same way and then irradiated for approximately 3-6 seconds until a maximum temperature of 45° C. was reached.

Standardized photographs were taken with Nikon CoolPix 3100 digital camera from 8 cm above the surface of the sample, 24 hours after the experiment and up to 7 subsequent days thereafter. Assessment of colony growth was made by converting standardized digital images into bitmap format, counting the amount of pixels per colony and converting this count to an average surface area in mm$^2$ using Microsoft™ Paint Program (Microsoft, Seattle, Wash.).

Figure 9:
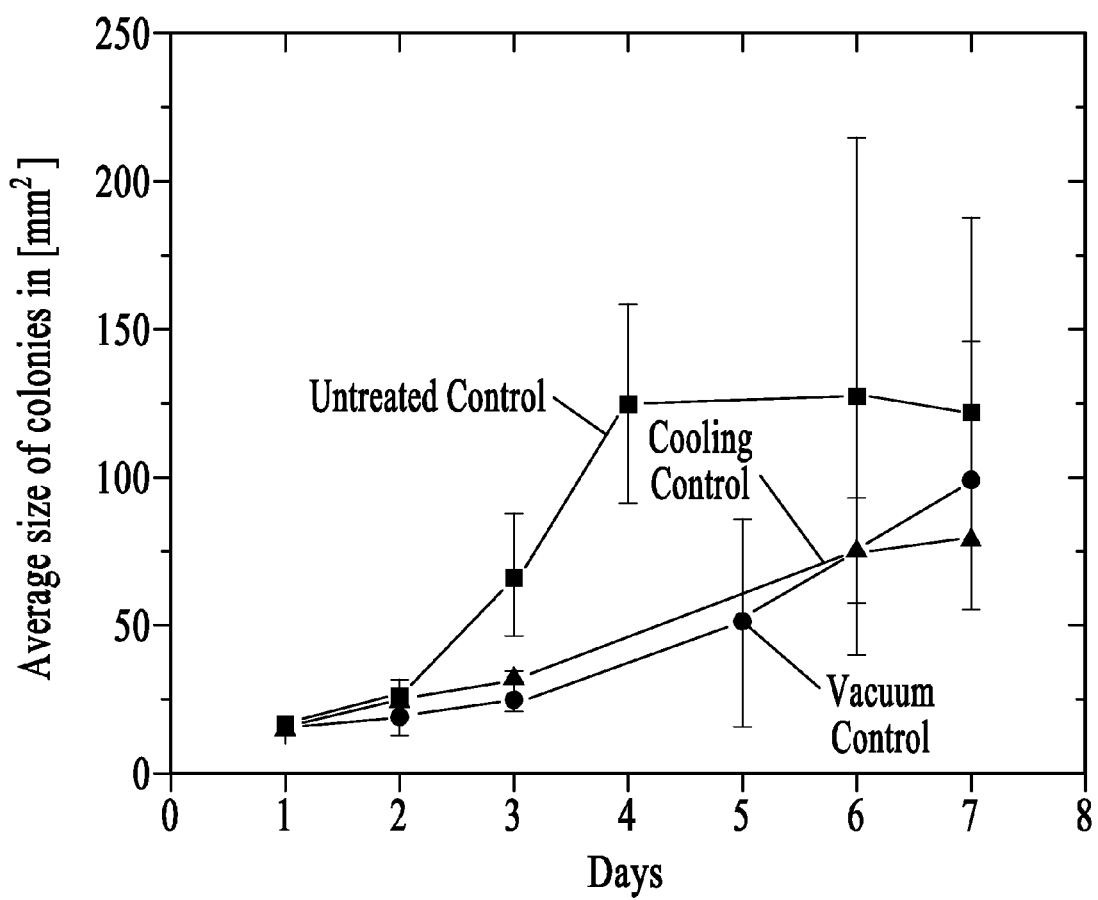
FIG. 9 is a representative chart showing a comparison of average size of control sample in $mm^2$.

Results:

FIG. 9 is a representative chart showing a comparison of average size of control sample in mm$^2$. In FIG. 9, squares indicate measurement of untreated control samples, circles indicate measurement of vacuum control samples and triangles indicate measurement of cooling control protocol samples. FIG. 9 shows preliminary results of the average growth rate and standard deviation of all control samples, which are those not irradiated. As shown in FIG. 9, the growth rate of the vacuum control samples and cooling control samples was slower than that of the untreated control samples. However, the trend of the vacuum control samples and cooling control samples toward the last days of this study seem to suggest that all control samples could have reached the same average size given long enough periods of time.

Figure 10:
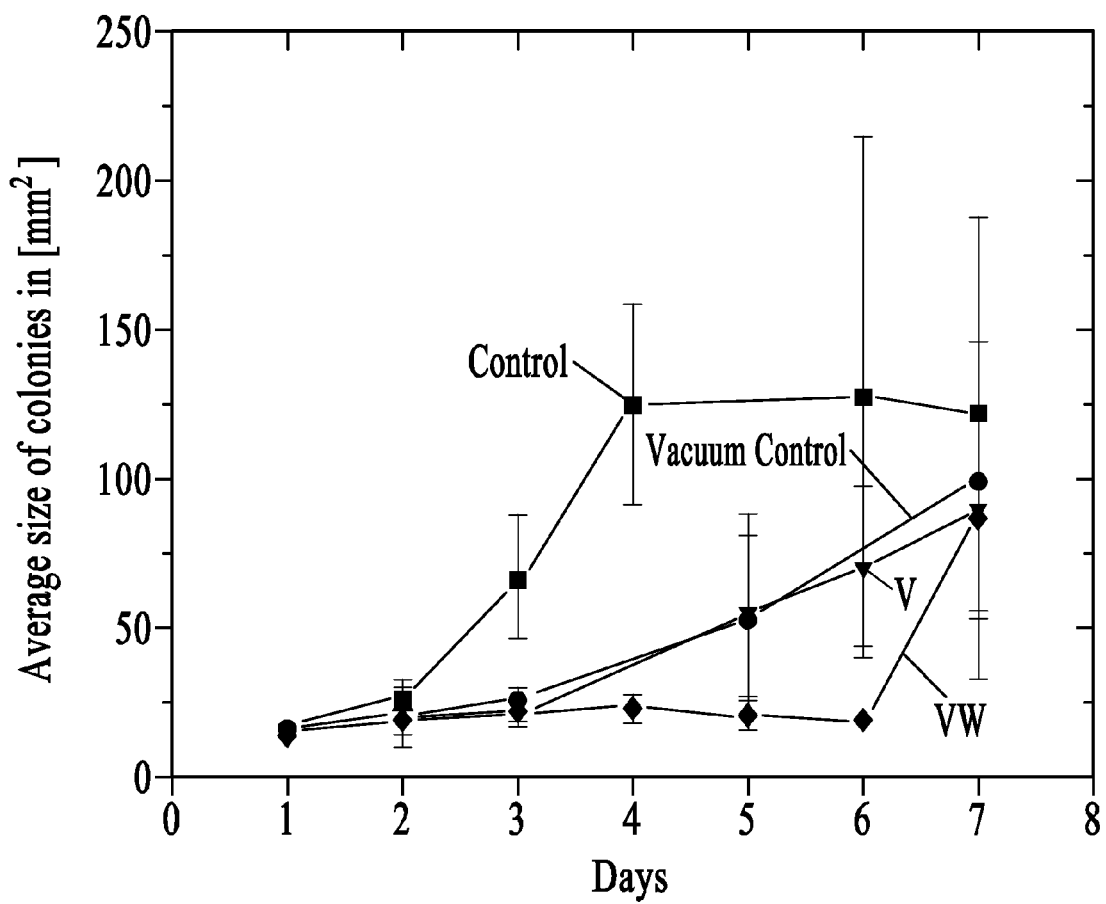
FIG. 10 is a representative chart showing a comparison of average size of colonies in mm² of four samples.

Vacuum Procedure (a) Results:

FIG. 10 is a representative chart showing a comparison of average size of colonies in mm$^2$ of four samples in the vacuum conditions (a) experiments. In FIG. 10, squares indicate measurement of untreated control samples, circles indicate measurement of vacuum control samples, upside town triangles indicate measurement of vacuum procedure without water dousing or hydration pre-procedurally samples (V) and diamonds indicate measurement of vacuum procedure after water dousing or hydration samples (VW). More specifically, the curve labeled "V" corresponds to the samples placed under vacuum, irradiated with 40-90 J, and left to grow. The curve labeled "VW" corresponds to those that were first doused or hydrated in water, placed in vacuum, and then irradiated with 40-90 J.

As shown in FIG. 10, while vacuum alone, as in vacuum control samples, seem to hamper the colony growth rate relative to untreated control samples, there was no significant difference between the vacuum control and (V) samples. Thus, irradiation alone does not appear to change the size of the colonies or growth rate once placed in vacuum. However, when the samples were doused with water and irradiated, as in (VW) samples, the growth rate was significantly suppressed for up until day 6, but for many of these samples, significant growth was observed by day 7, regardless of the energy input.

Figure 11A:
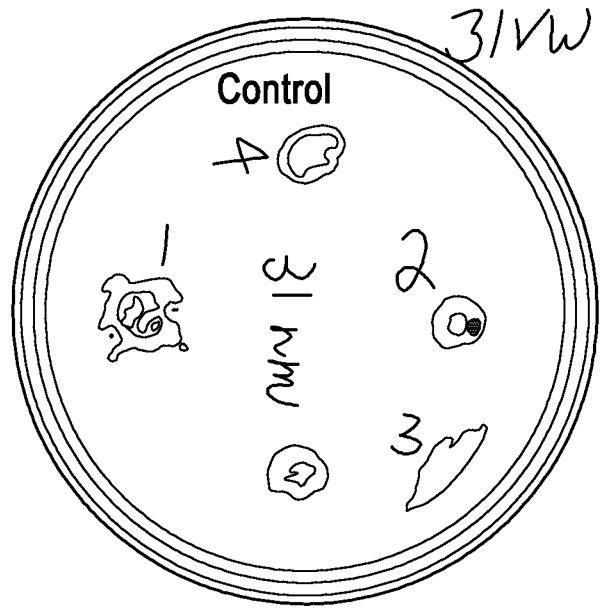
FIGS. 11A and 11B are representative graphics showing examples of medium affected by VW treatment.
Figure 11B:
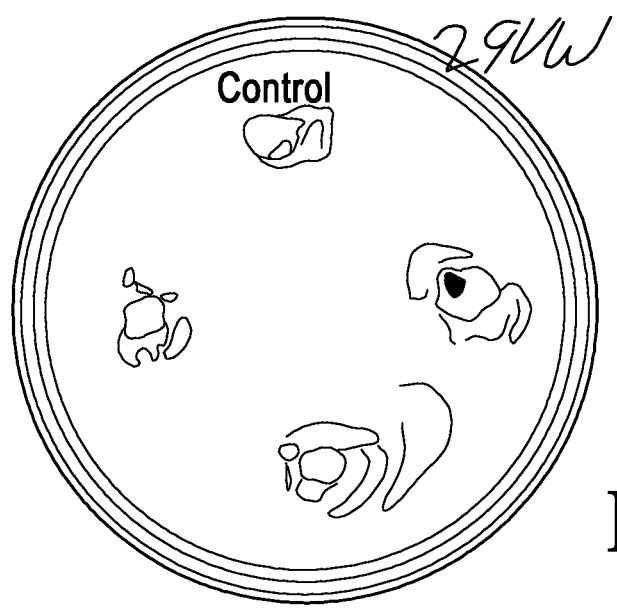

FIGS. 11A and 11B are representative illustrations showing examples of medium affected by (VW) treatment. FIG. 11A shows an example of normal medium after three days after (VW) treatment and FIG. 11B shows an example of medium that was adversely affected by the (VW) treatment shown in day three of post treatment. During the irradiation of many of the (VW) samples, it was observed that steam was formed and bubbles would form inside the medium and remained trapped for the duration of the experiment. The higher the energy input, the more steam and bubbles were produced. Also, a third of the Petri dishes used were affected in an unforeseen way. The consistency of the entire medium changed becoming thicker and grainy as shown in FIGS. 11A and 11B. This new medium greatly inhibited fungus growth.

Figure 12:
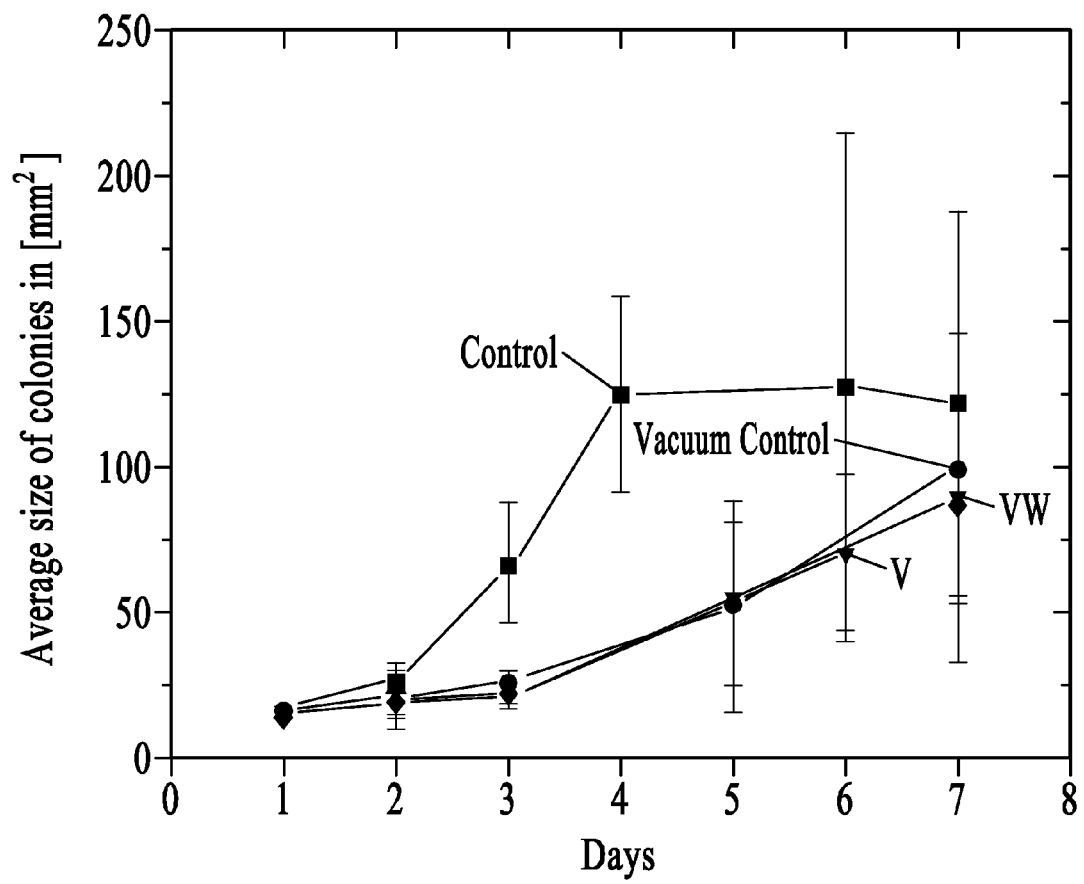
FIG. 12 is a representative chart showing a comparison of average size of colonies in mm² of four samples.

FIG. 12 is a representative chart showing a comparison of average size of colonies in mm$^2$ of four samples. When the Petri dishes that showed the thicker and grainy medium were removed from the analysis, the (VW) curve ended up matching the curves of the vacuum control and (V) samples, as best shown in FIG. 12.

Figure 13:
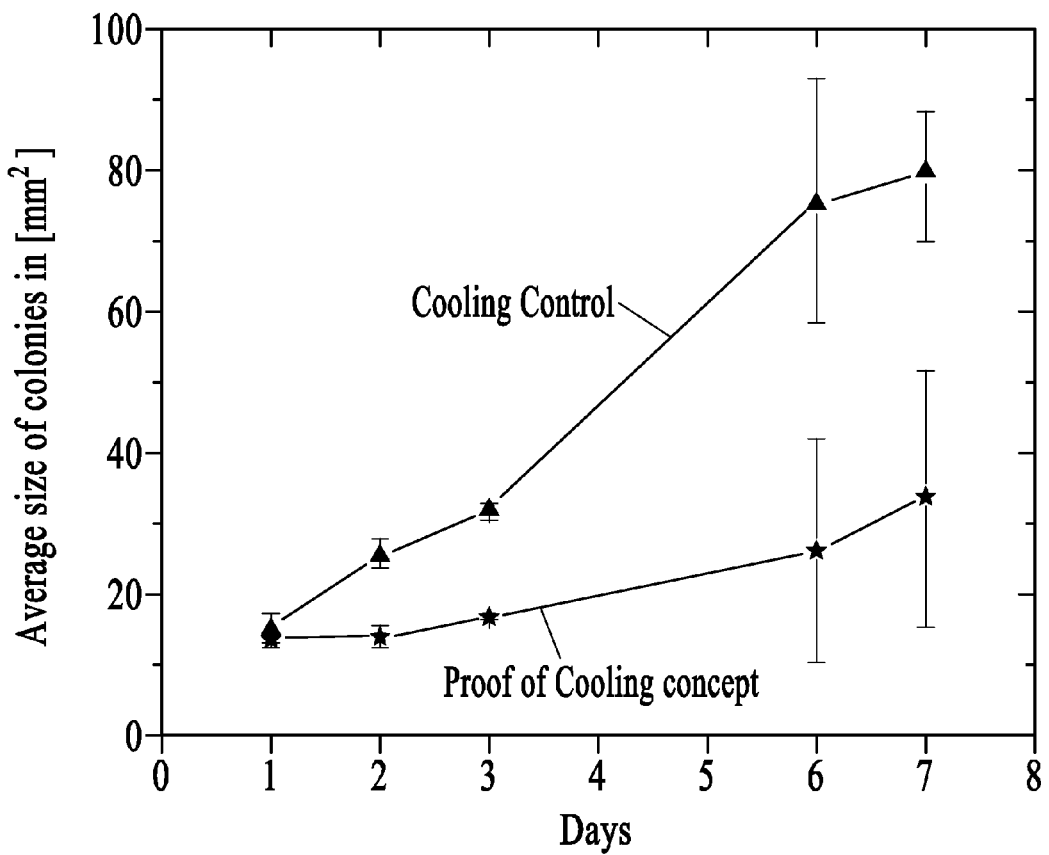
FIG. 13 is a representative chart showing a comparison of average size of colonies in mm² of two samples.

Thermal Shock Procedure (b) Results:

FIG. 13 is a representative chart showing a comparison of average size of colonies in mm$^2$ of two protocol cooling control samples. More specifically, triangles indicate measurement of protocol cooling control samples and stars indicate measurement of proof of cooling concept samples which were subjected to >100 J and the temperature 45-60° C. As shown in FIG. 13, this aggressive protocol proof of cooling concept was effective in hampering the growth of the colonies for all seven days. Only a few samples showed a small amount of growth over the week. It is unclear, however, if the effect on the growth rate is due to the temperature gradient, minimum and/or maximum temperature reached, or the total amount of energy administered by the laser. Clearly, this procedure would be unsuitable for clinical use due to the extreme temperatures involved.

Figure 14:
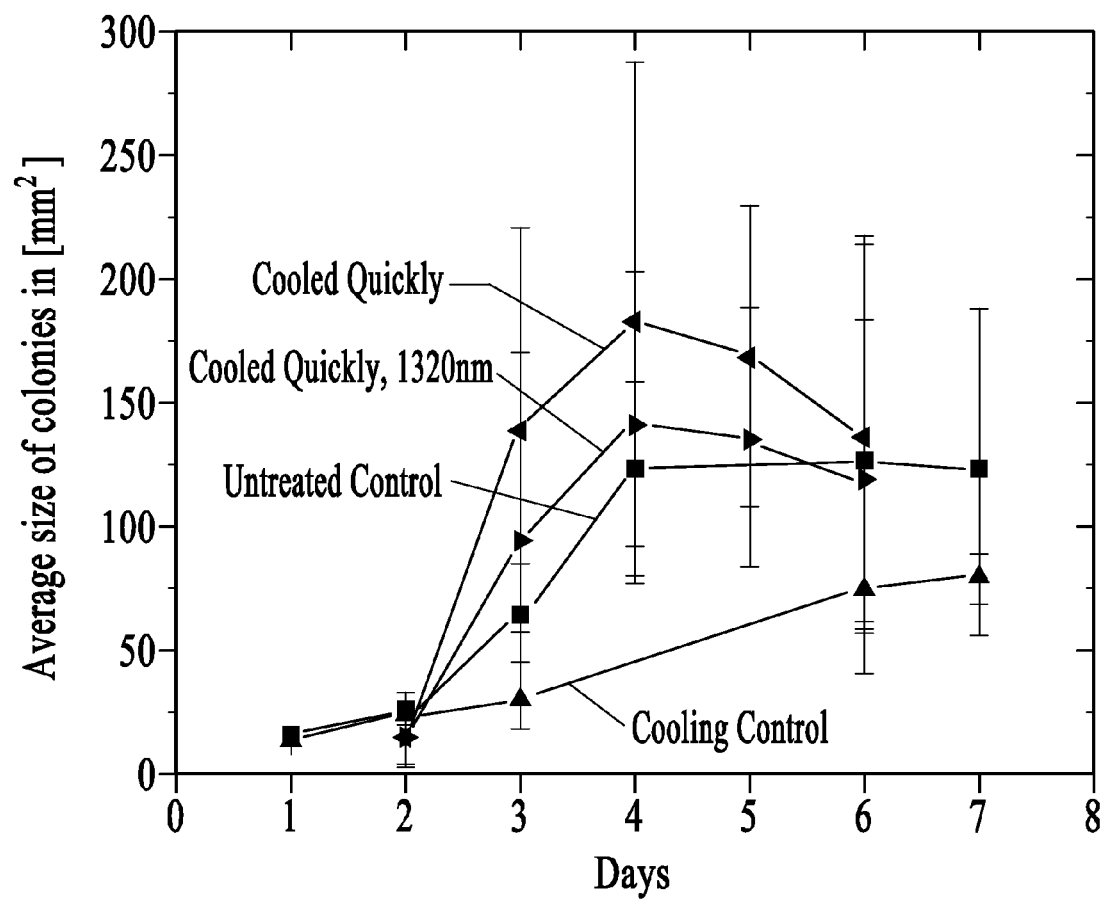
FIG. 14 is a representative chart showing a comparison of average size of colonies in mm² of four samples.
Figure 15:
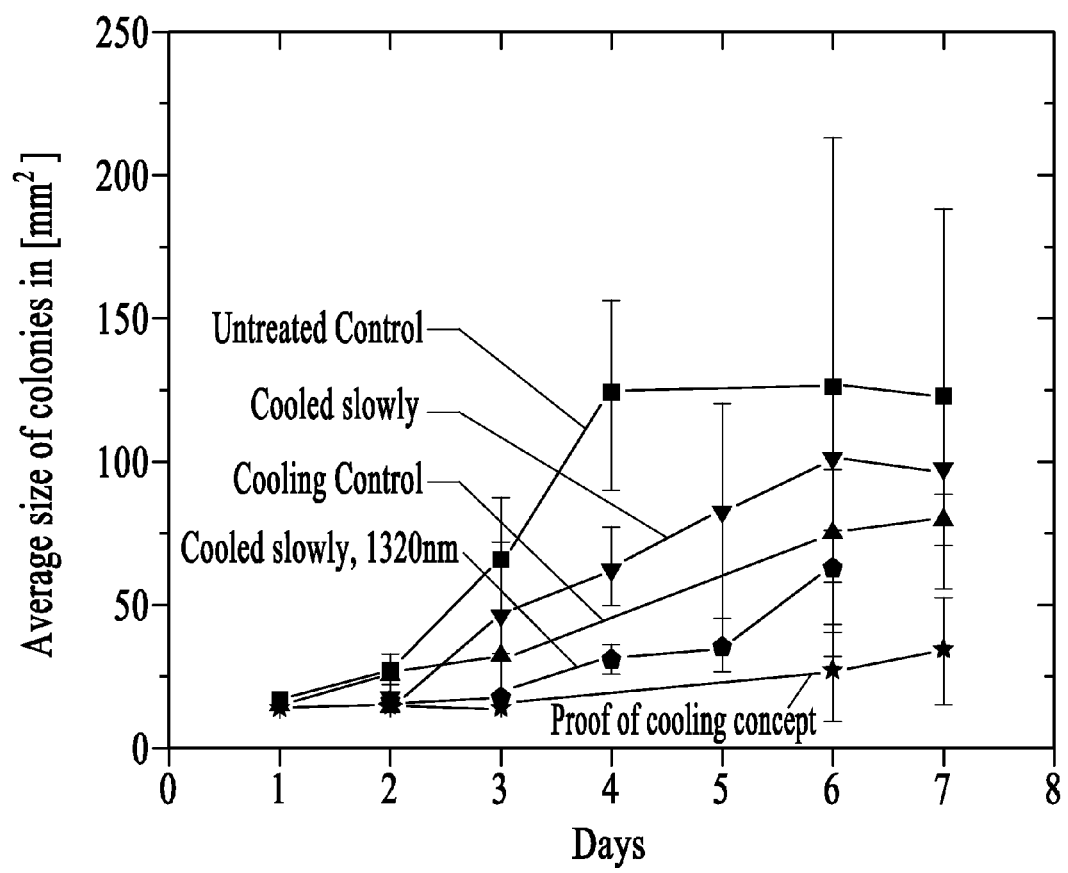
FIG. 15 is a representative chart showing a comparison of average size in mm² of a different set of four samples.

The results of the three cooling protocols with and without irradiation, along with the untreated and cooling controls are shown in FIGS. 14 and 15. More specifically in FIG. 14, squares indicate measurement of untreated control samples, triangles indicate measurement of cooling control samples, facing triangles indicate measurement of protocol quick cooled with irradiation samples and right facing triangles indicate measurement of protocol quick cooled without irradiation samples. And more specifically in FIG. 15, squares indicate measurement of untreated control samples, triangles indicate measurement of cooling control samples, stars indicate measurement of procedure proof of cooling concept samples, hexagon indicate measurement of protocol slow cooled with irradiation samples and upside down triangles indicate measurement of protocol slow cooled without irradiation samples.

Several observations can be made based on these experiments:

1. Relative to the untreated controls, the slow cooling procedure both with and without irradiation demonstrated a slower growth rate and smaller average size;

2. Both the irradiated and non-irradiated samples that were quick cooled demonstrated at least the same if not higher growth rates than the untreated control;
3. Laser irradiated samples show a reduced growth rate relative to their non-irradiate counterparts;
4. Relative to the cooling control, the slow cooled samples that were not irradiated had larger then average colony sizes. On the other hand, the slow cooled and irradiated samples had smaller colony sizes. All three showed similar growth rates; and
5. The results that showed the slowest growth rate were the proof of cooling concept. The second slowest were the cooled slowly, irradiated samples.

Discussion:

Vacuum Condition Procedure (a):

The objective of using vacuum pressure in conjunction with laser irradiation was, amongst other purposes, to take advantage of the reduced boiling temperature of water and either make more efficient use of the heat imparted via the laser or reduce the fluence required for fungus necrosis. The standard dry samples were very dry and while not overly desiccated, they did not have much excess water to alter with the vacuum pressures. Dehydrated conidia, one of the main types of spores that *T. rubrum* uses to infect and reproduce, can resist up to 124° C. for up to 3 minutes while still remaining largely viable, as disclosed in Schmit, J. C. et al., "Biochemical genetics of *Neurospora crassa* conidial germination", Microbiology and Molecular Biology Review, 1976. Thus, making the vacuum system no more effective then simply irradiating the samples while under standard temperature and pressure initial conditions, as best shown in FIG. 10. As best shown in FIGS. 11A, 11B and 12, water dousing or hydration appeared to have an important effect at first, but its effectiveness seem to be correlated with inexplicable changes we observed in the media which, once removed, appeared to have no effect. One of the factors that needs to be highlighted is that vacuum alone appeared to hamper the growth rate of the colonies with little to no effect from irradiation when the samples with deformed medium were removed, as best shown in FIG. 12, which leads us to believe that humidity may be a very important factor. In 1976, Schmit proposed that conidia viability was affected by humidity. Storing conidia at 100% humidity killed the samples after only nine days at 22° C. Other works indicated that *Trichophyton mentagrophytes*, the other main dermatophytes related to onychomycosis, has a very narrow humidity range of 95-98% and that different levels of humidity are better or worse for different stages of *T. mentagrophytes*—high humidity is necessary for arthrospore formation but reduced humidity necessary for maturation, as disclosed in Knight, A. G. "The effect of temperature and humidity on the growth of *Trichophyton mentagrophytes* spores on human stratum corneum in vitro", Clin Exp Dermatol, 1976. 1:p. 159-162. While *T. mentagrophytes* and *T. rubrum* are not the same, they are similar enough to warrant further studies investigating the effect of humidity and spore creation and growth.

In relation to our experiments, humidity comes into question when the effects of the (VW) technique are studied. The energy imparted to the sample during (V) and (VW) techniques was the same as the initial experiments of simple irradiation of a dry or wet sample with no other environmental factors (data not shown). Even though the energy was the same, the vacuum pressure reduces the boiling temperature of the water and thus it was reached sooner. This boiling, while enclosed in the small vacuum chamber, produced steam that would raise the relative humidity of the environment. Samples that received more energy also created more steam which may have further inhibited the growth rate of the samples. It is also possible that the humidity reached fits within the narrow band necessary for the efficient production of arthrospores while also destroying the main section of the fungus, thus minimizing the thermal effect that the laser irradiation would have on the growth rate. The current experiments cannot differentiate the effect of energy, overall temperature, or humidity from the results of the growth rate or colony size, so this should be investigated further.

As discussed above, there were many effects to the medium that could also change the outcome of the results. The water when placed on the sample did not only soak up into the fungus, but it also surrounded the fungus even going so far as to filter through the medium to get underneath the sample or in the crevices at the edge of the Petri dish. While irradiating the sample, the area directly around the sample would also become heated, as well as the water trapped within or around the medium. This caused the medium to change. Sometimes small bubbles would form in the medium that could not dissipate. For one third of the cases the medium was irrevocably changed for unknown reasons which greatly inhibited fungus growth as seen by the change between FIGS. 11A and 11B.

Thermal Shock Procedure (b):

*T. rubrum* is incredibly resistant to many extreme environments including heat, cold, and dryness. Dormant conidia and arthrospores, which are considered the main way that *T. rubrum* spreads and stays alive, have been known to survive at 4° C. for at least three years, with no morphological changes or mutations, as disclosed by Sinski et al., "Effect of storage temperature on viability of *Trichophyton mentagrophytes* in infected guinea pig skin scales, Journal of Clinical Microbiology, 1979. 10(b):p. 841. They can also withstand −70° C. for up to six months with no significant morphological changes, according to Baker M et al. and Espinel-Ingroff et al. studies. *T. rubrum* has also been known to be extremely resistant to heat. Mature conidia can withstand 55° C. for ten minutes with no loss in viability and more than 90% of dehydrated conidia can resist up to 124° C. for as much as three minutes, as disclosed in Schmit, J. C.'s publication. Dropping the initial cooling temperature to −20° C. and then raising it quickly to 45° C. is well within the range that many of the conidia can withstand, however, the quick cooling and heating rates may expose the fungus to extreme conditions that it may not be able to withstand. Further studies are required to address this issue.

The proof of cooling concept worked well because the samples were brought above 55° C. in a small amount of time and the sample was not completely desiccated due to the medium that it was growing on, making it more susceptible to the heating process. But it also explains why even those samples were not completely destroyed. All it takes is one viable conidia spore to create a whole new colony and the current procedure that is bounded by clinical pain boundaries is not enough to kill the entire sample. The samples that were more significantly affected out of the clinical temperature samples were the ones that were cooled slowly and then immediately irradiated to 45° C. The growth rate was about the same as the cooling control but the sample sizes were smaller overall for the first half of the week. Later, growth rate sped up and growth continued as normal. This may be an indicator that more of the sample was in a dormant stage due to the lower initial temperatures but that it was able to sufficiently recover and continue its growth. Multiple treatments following the same procedure or the introduction of topical or oral antifungal medications after initial thermal shock may continue to hamper and possibly eliminate the fungal growth.

The effects that were seen may also be due to the damage to the medium more than the sample itself. Freezing the Petri dish had the possibility of shrinking the entire plate of medium due to its high water content thereby inherently changing the fungi's ability to grow. For this experiment the samples that were dropped to only 0° C. were frozen as one dish while the samples that were reduced to −20° C. were frozen individually. Therefore, the shrinkage was only a possibility for the 0° C. experiments and not for the revised experiments thus mitigating the medium problem.

Conclusions:

Our results indicate that the vacuum condition (a) approach hampers the growth rate of fungi colonies relative to untreated control samples, especially the combination of water dousing or hydration prior to laser irradiation under vacuum conditions. Thermal shock (b) approach can also reduce the growth rate of fungi colonies when slow cooling is applied followed by rapid laser irradiation, while quick cooling preceding laser irradiation shows little effect.

Exposing fungi to vacuum alone appears to deter the fungus growth rate, even without laser irradiation. However, when fungus water dousing precedes laser irradiation, the growth rate is hampered even more. Overall, the vacuum samples showed some promise in that they did inhibit the growth of the samples but the results were not consistent and it is not entirely clear as to whether it is the fungus or the medium which is greater affected. Further studies must be done to distinguish the effects of humidity, as well as the effect of both thermal shock and vacuum combined and in multiple applications.

Most of the cooling results showed minimally effective at inhibiting the growth rate of *T. rubrum*. The best results so far are contained within the protocol proof of cooling concept samples but it was unclear whether or not it was the temperature gradient, maximum temperature, or amount of energy that had the dominant effect. The protocol cooling experiments that dropped the initial cooling temperature to −20° C. recreated the same temperature gradient as the proof of cooling concept samples but the results were universally worse producing a faster growth rate and larger sample size. This ruled out the temperature gradient, thus leaving the maximum temperature or the total amount of energy as the only feasible parameters to explain the difference. While the quick cooling samples at −20° C. produced unfavorable results, the results of the slow cooled, 1320 samples were promising. They reduced the growth rate and colony size beyond that of the cooling control while still staying within suitable temperature ranges for clinical use. The combination of thermal shock with vacuum or topical chemicals to improve upon the current results should be investigated in the future.

Since laser heating is still the underlying procedure, studies were initiated aimed at characterizing optically, both healthy and diseased human nails.

Figure 16A:
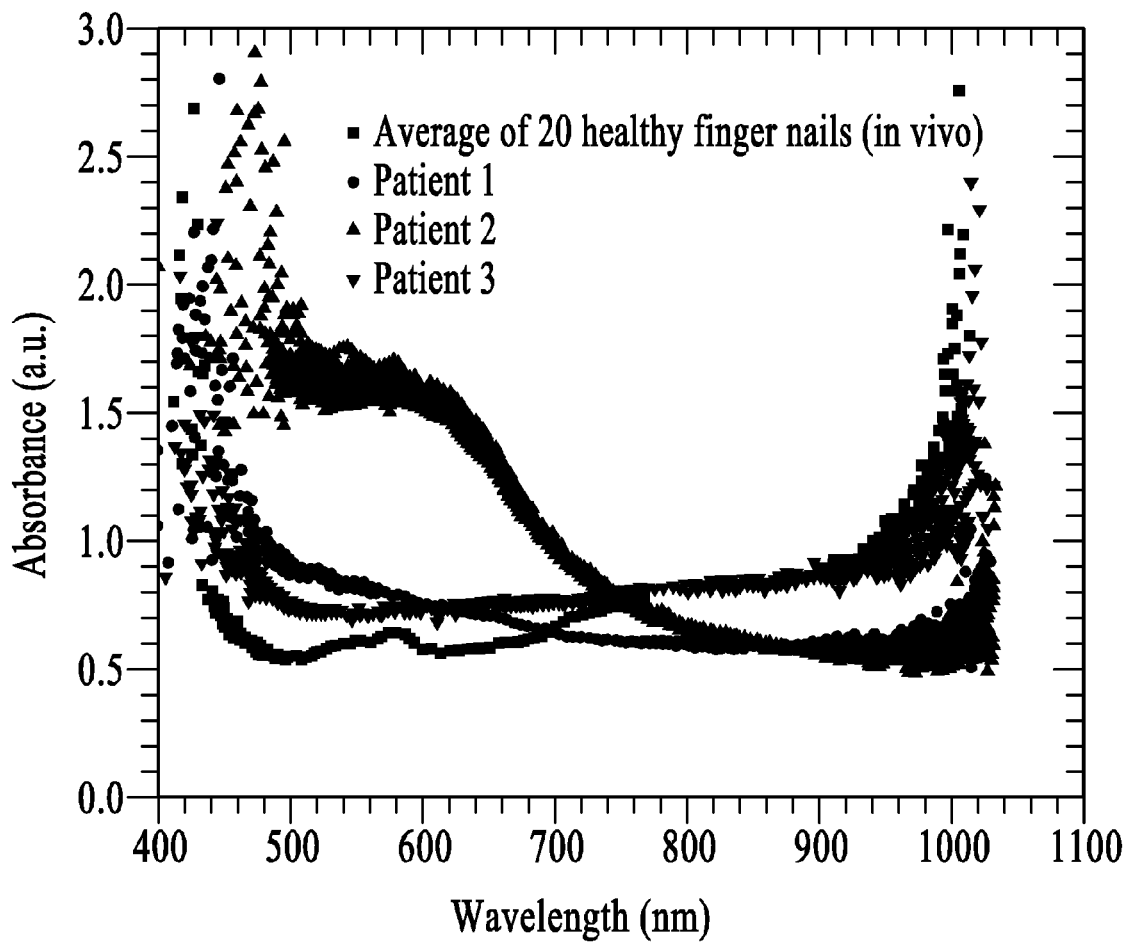
FIG. 16A is a representative graphic showing the appearance of 20 healthy in-vivo finger nails.

FIG. 16A shows the absorbance spectra of the average of twenty healthy finger nails and three diseased human toe nails, the apparent absorbance was obtained from reflectance measurements as the negative of the logarithm base 10 of the reflectance. These optical measurements could be used to determine which wavelength would be better absorbed by the diseased nail and use that wavelength to increase the nails temperature thus affecting more of the fungus overall and having a better chance to affect the fungus trapped on the edges of the nail or inside the nail itself. The difference in the absorbance spectrum between diseased nails could relate to different subtypes of onychomycosis or different stages of the disease, a nail in an advanced stage of onychomycosis is thicker and more opaque than a nail in an earlier stage of the disease, this thickness and opaqueness can be seen as an increase in absorbance in the visible portion of the spectrum as can be seen in the absorbance spectrum of Patient 2 in FIG. 16A.

Figure 16D:
FIGS. 16 B, C and D are representative graphics showing the appearance of diseased, ex-vivo toe nails, with FIG. 16B corresponding to circles, with FIG. 16C corresponding to triangles up, and with FIG. 16D corresponding to triangles down.
Figure 16C:
Figure 16B:
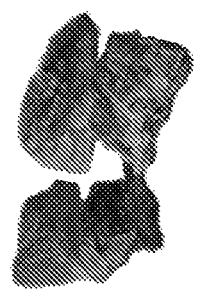

FIGS. 16 B, C and D are representative graphics showing the appearance of diseased, ex-vivo toe nails, with FIG. 16B corresponding to circles, with FIG. 16C corresponding to triangles up, and with FIG. 16D corresponding to triangles down.

Experiment IV

March 2010

Summary:

In this paper, we present preliminary results using the CoolTouch® 1320 nm mid-infrared CoolBreeze™ laser on patients to treat toenails that have demonstrated dermatophyte infections resulting in onychomycosis. Fungal infection was determined by the investigator pre-treatment. Toes were treated a minimum of two times at separate sessions with a minimum of 4-week intervals. There were 38 patients with a total of 54 toes treated. All subjects tolerated the treatments without anesthesia with one subject reporting an adverse event complaining of a localized, sharp pain like sensation that resolved within two months. Forty-three out of 54 (79.6%) toes treated showed a measurable increase in clear nail area. Improvement in the areas of clear nail growth was measured from 30 to 180 days post the final treatment.

Background:

Organisms that cause onychomycosis can invade both the nail bed and the nail plate. Dermatophytoses of the fingernails and toenails, in contrast to those at other body sites, are particularly difficult to eradicate with drug treatment. This is the consequence of factors intrinsic to the nail—the hard, protective nail plate, sequestration of pathogens between the nail bed and plate, and slow growth of the nail, as well as of the relatively poor efficacy of the early pharmacologic agents.

Study Rationale:

The efficacy of current treatment options, including topical, oral, mechanical and chemical therapies or a combination of these modalities is low. Topical drug treatment for onychomycosis is not usually successful because the drugs are unable to penetrate the nail plate and rapid recurrence can occur after discontinuing use. Oral antifungal agents are more effective although more toxic with a significant risk of liver toxicity, prolonged loss of taste, and life threatening drug interactions. Fungal resistance can occur when the oral antifungal agents are used on a long-term basis. Topically applied antifungal drugs may work somewhat better adjunctive to surgical removal or chemical dissolution of the nail plate. Yet, this often ineffective and traumatic procedure leaves the subject without a nail for months at risk for re-infection. The purpose of this study is to evaluate feasibility of the use of the CoolTouch® CT3P CoolBreeze™ laser to treat distal onychomycosis of the toenails.

Device Description:

The CoolTouch® CT3P CoolBreeze™ 1320 nm 18 W pulsed Nd:YAG laser is an FDA (K043046) cleared device and is indicated for use in dermatology for incision, excision, ablation and vaporization with hemostasis of soft tissue.

The unique handpiece design of the CoolTouch® laser allows the operator to maintain a constant distance from the area to be treated resulting in constant and uniform energy delivery. Treatment spot size is adjustable from 3 mm to 10 mm allowing pre-selection of the optimal spot size for the nail being treated. The energy delivered to the toenail can be adjusted by the selecting the desired level of watts (1.5 W to 12 W) with a push of a single control panel key. The CT3P CoolBreeze™ laser has a unique thermal sensing mechanism design to control the amount of energy delivered to the toenail by presetting the desired end target temperature. In addition, patient comfort is assured by a spray of a cooling agent when the target temperature is reached. Unlike other laser systems, having the fiber enclosed and terminated in the handpiece means that the fiber does not need cleaving during or after the laser procedure.

Study Design:

Thirty-eight volunteer subjects were recruited in a private podiatric practice. All of the subjects signed informed consent forms. Subjects were of either sex, greater than 18 years of age and determined to have subungual onychomycosis by the primary investigator.

Subjects were excluded from the study if they were pregnant, had a history of any treatment for onychomycosis within 3 months of the study enrollment date, had prior skin treatment with a laser or other devices on the same treated areas within 6 months of initial treatment, had prior use of topical medications (especially corticosteroids) in the treatment area within 2 weeks of the study period or systemic corticosteroids within 6 months of study enrollment or during the course of the study. Any condition which, in the investigator's opinion, would make it unsafe; for the subject or for the study personnel; to participate in this research study.

Each treated area was cleaned before treatment using alcohol-free agents to ensure that any perfumes, cosmetics, or lotions were removed. Nails were debrided pretreatment. Photographs for the evaluation were taken pre-treatment. The laser procedures were performed in the identified treated areas and all laser settings, spot size, watts, target temperature, cooling duration and total energy delivered were recorded at each laser treatment session. Patients were instructed to follow-up with daily foot care, applying an antifungal cream and scrubbing the toenails with soap/bleach solution, such as Pedinol®.

In addition, at the four and twelve and twenty-six week follow-up visits the following parameters were assessed and documented:
1. Photography of treated toe and foot;
2. KOH testing for dermatophyte infection;
3. Subject's self-reported level of pain or discomfort;
4. Subject's satisfaction with treatment;
5. Subject's self-reported level of improvement; and
6. Adverse events will be assessed, with continued monitoring and evaluation at subsequent visits.

Results:

Discomfort and pain levels were assessed immediately post treatment #1 and treatment #2 and at 1 week post last laser treatment. Pain and discomfort were graded on a 1 to 5 scale by the patient with 1 being no pain and 5 as severe pain. Immediately post laser treatment #1, patients reported a cumulative value of 1.8; post treatment #2 the calculated value was 1.9. Perceived pain and discomfort was reported to be between no pain and slight pain with no patients reporting a value higher than 3 (mild pain).

The investigator reported, by visual assessment, a positive response demonstrating a 79.6% increase in clear nail growth as compared to baseline photographs in the group of laser treated toes. Patient satisfaction (1—not satisfied to 5—extremely satisfied) in the reporting group at week 4 was 3.4, at week 12 the reported value increased to 3.6 resulting in a satisfaction level between satisfied to very satisfied. This patient subset showing improvement; as determined by the investigator; reported a 100% agreement with this determination.

Only one adverse event was reported; a localized, sharp pain like sensation in the large toe that resolved within two months.

Discussion:

In this early assessment of the CoolTouch® CT3P CoolBreeze™ 1320 nm laser for the treatment of onychomycosis, positive results are seen in clear nail plate increase in nearly 80% of the toenails treated. Unlike prior drug studies, no attempt was made to narrow the cohort of patients by selective eliminating those patients with proximal infections and nail matrix involvement, the very difficult to treat patient group usually non-responsive to pharmacologic agents. A two or three laser treatment regimen allows much higher patient compliance with the treatment protocol, very high patient safety with minimal or no side effects. Documented high patient satisfaction with minimal patient reported pain or discomfort suggests a safe and tolerable procedure. In addition, using the CoolTouch® CT3P CoolBreeze™ laser the procedure can be performed in less than 15 minutes; total treatment time for both feet and all toes with multiple passes; and allows effective utilization of valuable physician time.

Improved nail clearing demonstrated with these preliminary results support the hypotheses that the 1320 nm wavelength, using controlled energy delivery and a cooling spray is an effective treatment modality that inhibits or destroys the dermatophyte pathogens that cause onychomycosis resulting in high patient satisfaction. These findings strongly suggest comparable results with the other studies published and allow for greater physician choice in the equipment needed for the treatment of onychomycosis.

Concurrently-owned U.S. Pat. No. 5,820,626 entitled COOLING LASER HANDPIECE WITH REFILLABLE COOLANT RESERVOIR, U.S. Pat. No. 5,976,123 entitled HEAT STABILIZATION, U.S. Pat. No. 6,451,007 entitled THERMAL QUENCHING OF TISSUE, U.S. Pat. No. 7,122,029 entitled THERMAL QUENCHING OF TISSUE, U.S. Pat. No. 6,413,253 entitled SUBSURFACE HEATING OF MATERIAL, U.S. Pat. No. 6,273,885 entitled HANDHELD PHOTOEPILATION DEVICE METHOD and U.S. Pat. No. 7,217,265 entitled TREATMENT OF CELLULITE WITH MID-INFRARED RADIATION are hereby incorporated herein in their entireties in regards to their teaching of methods and apparatus for cryogenic cooling as part of an overall medical, dermatological and/or aesthetic treatment.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method of treating microbial infections in the nail of a toe or a finger, the method comprising the steps of: sealing the site of microbial infection within a vacuum chamber that fits over a toe or finger, thus creating a sealed chamber surrounding the toe or finger, wherein the vacuum chamber made of a material transparent to infrared radiation; irradiating the microbes through the transparent vacuum chamber with infrared radiation; and inducing mechanical damage to the site of the microbial infection by applying low pressures and temperatures between 45 degrees Celsius and 60 degrees Celsius.

2. The method of claim 1, further including the step of using pulsed radiation with a wavelength that is selectively absorbed by the microbes and with a pulse length that is chosen to match the thermal diffusion properties of the microbe.

3. The method of claim 1, further comprising the step of introducing gold nanoparticles (GNPs) or other particle seeds to create a rapid and violent thermoelastic expansion or cavitation of the microbial infection, thereby increasing the disinfection efficiency during laser irradiation.

4. The method of claim 1, wherein the microbial infection is a toenail fungus or infection.

5. The method of claim 1, further comprising the step of hydrating the site of microbial infection prior to irradiating with infrared radiation.

6. The method of claim 5 further comprising the step of hydrating the toe or finger nail by bathing in warm water.

7. The method of claim 1, wherein the step of irradiating the microbe with infrared radiation is performed using laser energy having a wavelength between 1450 nm and 1550 nm.

8. The method of claim 1, wherein the step of irradiating the microbe with infrared radiation is performed using laser energy having a wavelength of 1470 nm.

9. The method of claim 1, wherein the vacuum chamber further comprises (I) an open end having a circular sealing member, (ii) a central tubular section, and (iii) a sealed end, the method further comprising the step of sealing the vacuum chamber around the site of microbial infection with the circular sealing member to create a vacuum therein.

* * * * *